(12) United States Patent
Beinat et al.

(10) Patent No.: US 10,675,366 B2
(45) Date of Patent: *Jun. 9, 2020

(54) IMAGING TUMOR GLYCOLYSIS BY NON-INVASIVE MEASUREMENT OF PYRUVATE KINASE M2

(71) Applicant: The Board of Trustees of the Leland Stanford Junior University, Palo Alto, CA (US)

(72) Inventors: Corrine Gaye Beinat, San Ramon, CA (US); Israt Shamima Alam, Mountain View, CA (US); Michelle L. James, Menlo Park, CA (US); Sanjiv S. Gambhir, Portola Valley, CA (US); Ananth Srinivasan, El Dorado Hills, CA (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 9 days.

This patent is subject to a terminal disclaimer.

(21) Appl. No.: 15/674,701

(22) Filed: Aug. 11, 2017

(65) Prior Publication Data

US 2018/0043040 A1 Feb. 15, 2018

Related U.S. Application Data

(60) Provisional application No. 62/374,088, filed on Aug. 12, 2016.

(51) Int. Cl.
| | | |
|---|---|---|
| *A61K 51/00* | (2006.01) | |
| *A61K 51/04* | (2006.01) | |
| *C07D 295/26* | (2006.01) | |
| *C07B 59/00* | (2006.01) | |
| *A61M 36/14* | (2006.01) | |

(52) U.S. Cl.
CPC ........ *A61K 51/0459* (2013.01); *C07B 59/002* (2013.01); *C07D 295/26* (2013.01); *A61K 2123/00* (2013.01); *C07B 2200/05* (2013.01)

(58) Field of Classification Search
None
See application file for complete search history.

(56) References Cited

U.S. PATENT DOCUMENTS

2012/0108631 A1* 5/2012 Becker ................ C07D 209/08
514/312
2016/0158389 A1* 6/2016 Witney ............ A61K 51/0459
424/1.89

FOREIGN PATENT DOCUMENTS

WO WO-2012151450 A1 * 11/2012 ......... A61K 31/4704

OTHER PUBLICATIONS

Boxer et al. (J. Med. Chem. 2010, 53, 1048-1055).*

* cited by examiner

*Primary Examiner* — Michael G. Hartley
*Assistant Examiner* — Melissa J Perreira
(74) *Attorney, Agent, or Firm* — Thomas | Horstemeyer, LLP

(57) ABSTRACT

The present disclosure provides a positron emission tomography (PET)-detectable 1-((2-fluoro-6-[$^{18}$F]fluorophenyl) sulfonyl)-4-((4-methoxyphenyl)sulfonyl)piperazine ([$^{18}$F] DASA-23) probe that can selectively bind to the pyruvate kinase variant M2 (PKM2) found in cancer cells, such as of human glioma. Given the importance of PKM2 in the regulation of tumor metabolism, there is an on-going need to non-invasively measure its expression through the development of PKM2-specific radiopharmaceuticals. Precursors useful for the synthesis of the radiolabeled [$^{18}$F]DASA-23-PKM2-specific probe and related compounds, and their methods of synthesis, are provided. Since the half-life of the $^{18}$F isotope is approximately 110 min, it is advantageous for a practitioner to attach the radionuclide to the precursor shortly before administration. Therefore, a precursor compound suitable for receiving the radionuclide and capable of specifically binding to the PKM2 variant can be provided.

24 Claims, 10 Drawing Sheets

IMAGING TUMOR GLYCOLYSIS BY NON-INVASIVE MEASUREMENT OF PYRUVATE KINASE M2

CROSS-REFERENCE TO RELATED APPLICATION

This application claims priority to and the benefit of U.S. Provisional Application 62/374,088 titled "IMAGING TUMOR GLYCOLYSIS BY NON-INVASIVE MEASUREMENT OF PYRUVATE KINASE M2" filed Aug. 12, 2016, the entire disclosure of which is incorporated herein by reference.

TECHNICAL FIELD OF THE DISCLOSURE

The present disclosure is generally related to probes and methods advantageous for detecting pyruvate kinase M2 in cells. The present disclosure is further generally related to methods of imaging tumors by detecting pyruvate kinase M2 activity using positron emission tomography (PET)-specific probes.

BACKGROUND

To sustain rapid cell division and growth, tumors undergo metabolic reprogramming. Understanding how cancer cells adjust to the metabolic needs of their unique biology has been a focus of cancer research for many years (Cairns et al., (2011) *Nat. Rev. Cancer* 11: 85-95). The concept of metabolic adaptation was first reported by Otto Warburg over 80 years ago, after he observed that cancer cells exhibited enhanced consumption of glucose and production of lactate in comparison to normal tissue, even under aerobic conditions (Warburg O (1956) *Science* 123: 309-314). This phenomenon became known as the Warburg effect. While normal, differentiated cells maximize ATP production by mitochondrial oxidative phosphorylation of glucose under normoxic conditions, cancer cells produce substantially less ATP from glucose using aerobic glycolysis (Wong et al., (2013) *Int. J. Cell Biol.* 2013: 242513).

The enhancement in aerobic glycolysis combined with the dynamic processes in cancer cells enables glycolytic intermediates to be redirected for the biosynthetic production of cellular building blocks such as nucleotides, amino acids, and lipids, while still producing ATP (Wong et al., (2013) *Int. J. Cell Biol.* 2013: 242513), therefore fulfilling the requirements for macromolecular synthesis and energy production (Vander Heiden et al., (2009) *Science* 324: 1029-1033; Hsu & Sabatini (2008) *Cell* 134: 703-707). The Warburg effect has been extensively exploited clinically to detect tumors and their response to treatment by [$^{18}$F]FDG. [$^{18}$F]FDG PET non-invasively measures rates of glucose metabolism and is approved for the diagnosis of most cancers and has proven particularly useful as a staging and restaging tool that can guide patient care (Kelloff et al., (2005) *Clin. Cancer Res.* 11: 2785-2808; Sharma et al., (2004) *Radiographics* 24: 419-434). Since glucose metabolism is an essential cellular process, [$^{18}$F]FDG is not specific for malignant cells. Particularly in the brain, which has a high rate of glucose metabolism, and therefore a high physiological uptake of [$^{18}$F]FDG, it is extremely difficult to delineate brain tumor margins with [$^{18}$F]FDG PET imaging. There is a continuing need for PET imaging agents with selectivity for molecular processes unique to cancer cells.

Pyruvate kinase (PK) catalyzes the final and rate-limiting step in glycolysis, converting phosphoenol pyruvate (PEP) to pyruvate by transferring the high-energy phosphate group to adenosine diphosphate (ADP) and yielding ATP (Wong et al., (2013) *Int. J. Cell Biol.* 2013: 242513). Reduced PK activity results in a diminished production of pyruvate or prevention of the conversion of glucose to pyruvate, therefore enabling the accumulation of upstream glycolytic intermediates and shifting metabolism towards the anabolic phase. Cancer cells exploit this effect by primarily utilizing the PKM2 isoform of PK, whose activity can be dynamically controlled between the less active PKM2 dimer and the highly active PKM2 tetramer (Christofk et al., (2008) *Nature* 452: 230-233).

PKM2 is found in most cells with the exception of adult muscle, brain, and liver and is preferentially expressed in all cancers to date (Christofk et al., (2008) *Nature* 452: 230-233). The dynamic equilibrium between the dimeric and tetrameric states of PKM2 enables proliferating tumor cells to regulate their needs for anabolic and catabolic metabolism. The alternative splicing of PKM2 is regulated by oncogenes c-Myc and HIF-1 (Chaneton & Gottlieb (2012) *Trends Biochem. Sci.* 37: 309-316), with the quaternary structure of PKM2 regulated by the glycolytic intermediate fructose 1,6-biphosphate (FBP) and growth factor signalling (Bailey et al., (1968) *Biochem J.* 108: 427-436; Christofk et al., (2008) *Nature* 452: 181-186).

The expression of PKM2 has been shown to be increased in a diverse range of human cancers, including lung, breast, prostate, blood, cervix, kidney, bladder, and colon, compared to the matched normal tissues (Bluemlein et al., (2011) *Oncotarget* doi:10.18632/oncotarget.278). PKM2 expression is linked to increased uptake of glucose, enhanced lactate production, and a decrease in oxygen consumption, effects which can be reversed by genetic modifications to replace PKM2 expression with PKM1 (Christofk et al., (2008) *Nature* 452: 230-233, Luo & Semenza (2012) *Trends Endocrinol. Metab.* 23: 560-566). The Warburg effect is, therefore, partly mediated by PKM2 expression, with the high expression of dimeric PKM2 in cancer cells contributing to anabolic glucose metabolism, promoting macromolecular biosynthesis and benefiting cancer cell proliferation and growth (Luo & Semenza (2012) *Trends Endocrinol. Metab.* 23: 560-566).

In recent years, PKM2 has been explored as a potential target for cancer therapy through the development of small molecule activators that promote and stabilize active tetramer formation (Boxer et al., (2010) *J. Med. Chem.* 53: 1048-1055; Israelsen et al., (2013) *Cell* 155: 397-409). Multiple classes of PKM2 activators have been developed, and representative examples are shown in FIG. 6. These examples include a series of N—N'-diaryl sulfonamides (1), thieno[3,2-b]pyrrole[3,2-d]pyridazinones (2, 3), 1-(sulfonyl)-5-(arylsulfonyl)indoline (4), 2-((1H-benzo[d]imidazole-1-methyl)-4H-pyrido[1,2-a]pyrimidin-4-ones (5), 3-(trifluoromethyl)-1H-pyrazole-5-carboxamide (6), and more recently 7-azaindole derivative (7). Clinically relevant imaging agents for the direct, non-invasive measurement of cancer-specific biomarkers are a topic of extreme interest and importance, particularly for brain tumors. Although [$^{18}$F]FDG PET is approved for use for the diagnosis of most cancers, a high background uptake by surrounding healthy tissue can mask tumor uptake, for example, in the normal brain (Phelps & Mazziotta (1985) *Science* 228: 799). Consequently, the non-invasive measurement of PKM2 has the potential to play an important role in the detection and management of malignancies where [$^{18}$F]FDG fails.

SUMMARY

The present disclosure encompasses embodiments of a non-invasive method for the detection of PKM2 expression in subcutaneous and orthotopic tumors through positron emission tomography (PET) imaging of the PKM2 activator, [$^{18}$F]DASA-23. [$^{18}$F]DASA-23 cell uptake correlates with PKM2 protein expression in cultured tumor cells and orthotopic tumors are delineated from the surrounding normal brain tissue in vivo. PET/MR imaging confirmed correspondence of the [$^{18}$F]DASA-23 signal with the location of intracranial tumors. Together, these data provide the basis for imaging agents that target this important gatekeeper of tumor glycolysis.

Accordingly, one aspect of the disclosure encompasses embodiments of a pyruvate kinase M2 activator precursor having the formula I:

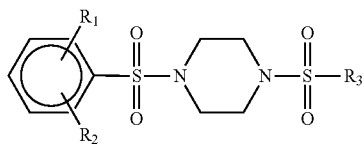

I wherein: at least one of $R_1$ and $R_2$ can be $NO_2$; when $R_2$ is $NO_2$, $R_1$ is F or $NO_2$; and $R_3$ is a substituted aryl, naphthalene, or 1,4 benzodioxane.

In some embodiments of this aspect of the disclosure, $R_3$ can be an alkoxyphenyl or an aminophenyl.

In some embodiments of this aspect of the disclosure, $R_3$ is 4-methoxyphenyl, 4-ethoxyphenyl, 4-propoxyphenyl, or 4-aminophenyl.

In some embodiments of this aspect of the disclosure, the precursor has the formula II:

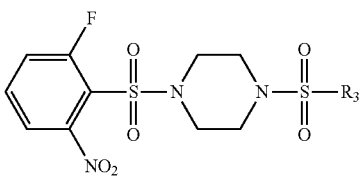

II wherein $R_3$ is a substituted aryl.

In some embodiments of this aspect of the disclosure, $R_3$ is 4-methoxyphenyl.

Another aspect of the disclosure encompasses embodiments of a Positron Emission Tomography (PET)-detectable probe having the formula III:

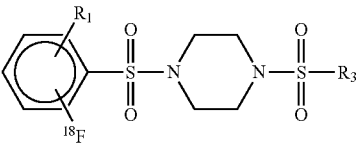

III wherein: $R_1$ is F or $^{18}$F; and $R_3$ can be a substituted aryl, naphthalene, or 1,4 benzodioxane.

In some embodiments of this aspect of the disclosure, $R_3$ is an alkoxyphenyl or an aminophenyl.

In some embodiments of this aspect of the disclosure, $R_3$ is 4-methoxyphenyl, 4-ethoxyphenyl, 4-propoxyphenyl, or 4-aminophenyl.

In some embodiments of this aspect of the disclosure, the probe has the formula IV:

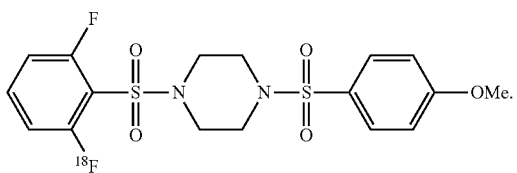

IV

Still another aspect of the disclosure encompasses embodiments of a pharmaceutically acceptable probe composition comprising a Positron Emission Tomography (PET)-detectable radiolabelled probe having the formula III:

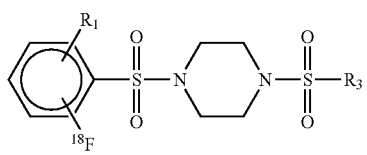

III wherein: $R_1$ is F or $^{18}$F; and $R_3$ can be a substituted aryl, naphthalene, or 1,4 benzodioxane.

In some embodiments of this aspect of the disclosure, the probe can have the formula IV:

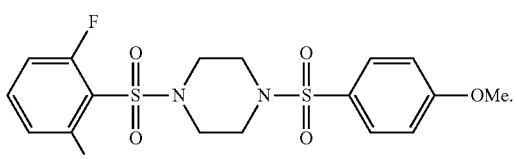

IV

In some embodiments of this aspect of the disclosure, the pharmaceutically acceptable probe composition can further comprise a pharmaceutically acceptable carrier.

Still another aspect of the disclosure encompasses embodiments of a method of generating a pyruvate kinase M2 activator precursor, wherein said precursor is 1-((2-fluoro-6-nitrophenyl)sulfonyl)-4-((4-methoxyphenyl)sulfonyl)piperazine (10) having the formula II:

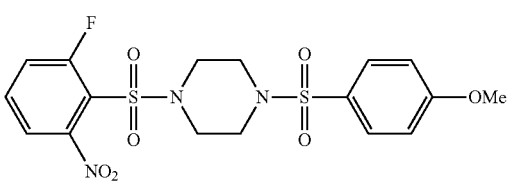

II the method comprising the steps of: (a) reacting 1-Boc-piperazine, trimethylamine and 4-methoxybenzenesulfonyl chloride to generate tert-butyl 4-((4-methoxyphenyl)sulfonyl)piperazine-1-carboxylate (8); (b) quenching the reaction of step (a) with saturated aqueous ammonium chloride and purifying the first product; (c) reacting the product of step (b) with trifluoroacetic acid to generate a TFA salt of 1-((4-methoxyphenyl)sulfonyl)piperazine (9); and (d) reacting the TFA salt of 1-((4-methoxyphenyl)sulfonyl)piperazine (9) product of step (c) with 2-fluoro-6-nitrobenzenesulfonyl chloride to generate 1-((2-fluoro-6-nitrophenyl)sulfonyl)-4-((4-methoxyphenyl)sulfonyl)piperazine (10) or with 2-bromo-6-fluorobenzenesulfonyl chloride to generate 1-((2-bromo-6-fluorobenzenesulfonyl)-4-((4-methoxyphenyl)sulfonyl)piperazine In some embodiments of this aspect of the disclosure, the step (d) can comprise reacting the TFA salt of 1-((4-methoxyphenyl)sulfonyl)piperazine (9) product of step (c) with 2-fluoro-6-nitrobenzenesulfonyl chloride to generate 1-((2-fluoro-6-nitrophenyl)sulfonyl)-4-((4-methoxyphenyl)sulfonyl)piperazine (10).

Still another aspect of the disclosure encompasses embodiments of a method of generating a radiolabelled probe, wherein the probe is 1-((2-fluoro-6-(fluoro-$^{18}$F)phenyl)sulfonyl)-4-((4-methoxyphenyl)sulfonyl)piperazine, said method comprising the steps: (a) fluoridating 4,7,13,16,21,24-hexaoxa-1,10-diazabicyclo[8.8.8]hexacosan (K2.2.2) with $^{18}$F; and (b) reacting 1-((2-fluoro-6-nitrophenyl)sulfonyl)-4-((4-methoxyphenyl)sulfonyl)piperazine (10) or 1-((2-bromo-6-fluorobenzenesulfonyl)-4-((4-methoxyphenyl)sulfonyl)piperazine with the fluoridated product of step (a), thereby obtaining 1-((2-fluoro-6-(fluoro-$^{18}$F)phenyl)sulfonyl)-4-((4-methoxyphenyl)sulfonyl)piperazine.

In some embodiments of this aspect of the disclosure, the step (b) can comprise reacting 1-((2-fluoro-6-nitrophenyl)sulfonyl)-4-((4-methoxyphenyl)sulfonyl)piperazine (10) with the fluoridated product of step (a), thereby obtaining 1-((2-fluoro-6-(fluoro-$^{18}$F)phenyl)sulfonyl)-4-(4-methoxyphenyl)sulfonyl)piperazine.

Still another aspect of the disclosure encompasses embodiments of a method of detecting a cell or a population of cells expressing pyruvate kinase M2, said method comprising: (i) contacting a cell or population of cells with a pharmaceutically acceptable PET-detectable radiolabelled probe composition comprising at least one probe having a radionuclide and having the formula:

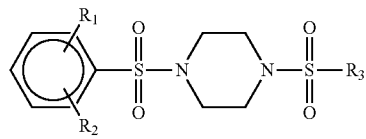

I wherein $R_2$ is $^{18}$F and $R_1$ can be F or $^{18}$F; and $R_3$ can be a substituted aryl, naphthalene, or 1,4 benzodioxane; and (ii) detecting pyruvate kinase M2-specific binding of the radionuclide-containing probe within the cell or population of cells by detecting the presence of the radionuclide in the cell or population of cells.

In some embodiments of this aspect of the disclosure, the probe can have the formula IV:

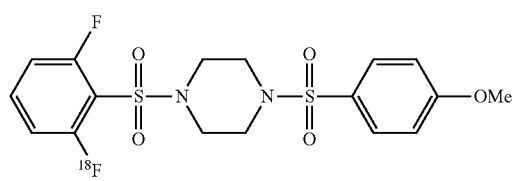

IV

In some embodiments of this aspect of the disclosure, the method can further comprise the step of delivering the pharmaceutically acceptable probe composition to a human or non-human animal.

In some embodiments of this aspect of the disclosure, in step (ii) of said method, the detection of the radionuclide can be by Positron Emission Tomography (PET).

Yet another aspect of the disclosure encompasses embodiments of a method of detecting in a human or non-human animal a localized population of cancer cells expressing pyruvate kinase M2 (PKM2), said method comprising the steps of: (i) administering to a human or non-human animal a pharmaceutically acceptable composition comprising a radiolabeled pyruvate kinase M2 (PKM2)-specific probe having the formula I:

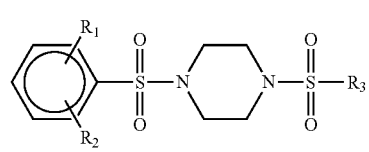

I wherein $R_2$ is $^{18}$F and $R_1$ is F or $^{18}$F; and $R_3$ is a substituted aryl, naphthalene, or 1,4 benzodioxane; and (ii) identifying a tissue in the animal or human host, wherein the amount of the detectable label in the tissue is greater than in other tissues of the host, thereby identifying a population of cancer cells expressing pyruvate kinase M2.

In some embodiments of this aspect of the disclosure, the probe can have the formula IV:

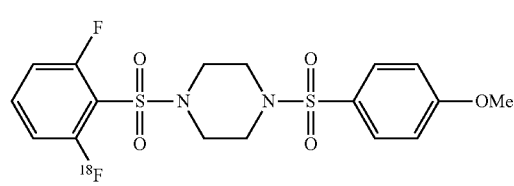

IV

In some embodiments of this aspect of the disclosure, the radiolabeled pyruvate kinase M2 (PKM2)-specific probe can be detected by Positron Emission Tomography (PET) scanning.

In some embodiments of this aspect of the disclosure, the tissue is a glioma of the brain.

The probes and the methods of use thereof are advantageous for the detection and imaging of tumors, and are especially useful for the detection and imaging of tumors such as gliomas of the brain since the probes are able to traverse the blood-brain barrier.

BRIEF DESCRIPTION OF THE DRAWINGS

Aspects of the present disclosure will be more readily appreciated upon review of the detailed description of its various embodiments, described below, when taken in conjunction with the accompanying drawings. The drawings are described in greater detail in the description and examples below.

FIG. 1A illustrates that pyruvate kinase catalyzes the final step of glycolysis, resulting in net ATP synthesis through the dephosphorylation of phosphoenolpyruvate. The pyruvate kinase M2 (PKM2) isozyme predominates in proliferating non-malignant and in tumor cells. Two quaternary PKM2 conformations exist as homo-dimeric or -tetrameric forms. Dimeric PKM2 has reduced affinity for phosphoenolpyruvate in comparison to the tetramer, with tumor PKM2 mainly present in the dimeric form, resulting in a buildup of glycolytic precursors for use in biosynthetic processes. Conversely, PKM2 is mostly present in the tetrameric form in non-malignant cells.

FIG. 1B illustrates that PKM2 conformation is governed by intracellular concentrations of fructose-1,6-bisphosphate, direct oncogene regulation, and pharmacologically through PKM2 activators.

DESCRIPTION OF THE DISCLOSURE

Figure 1A:
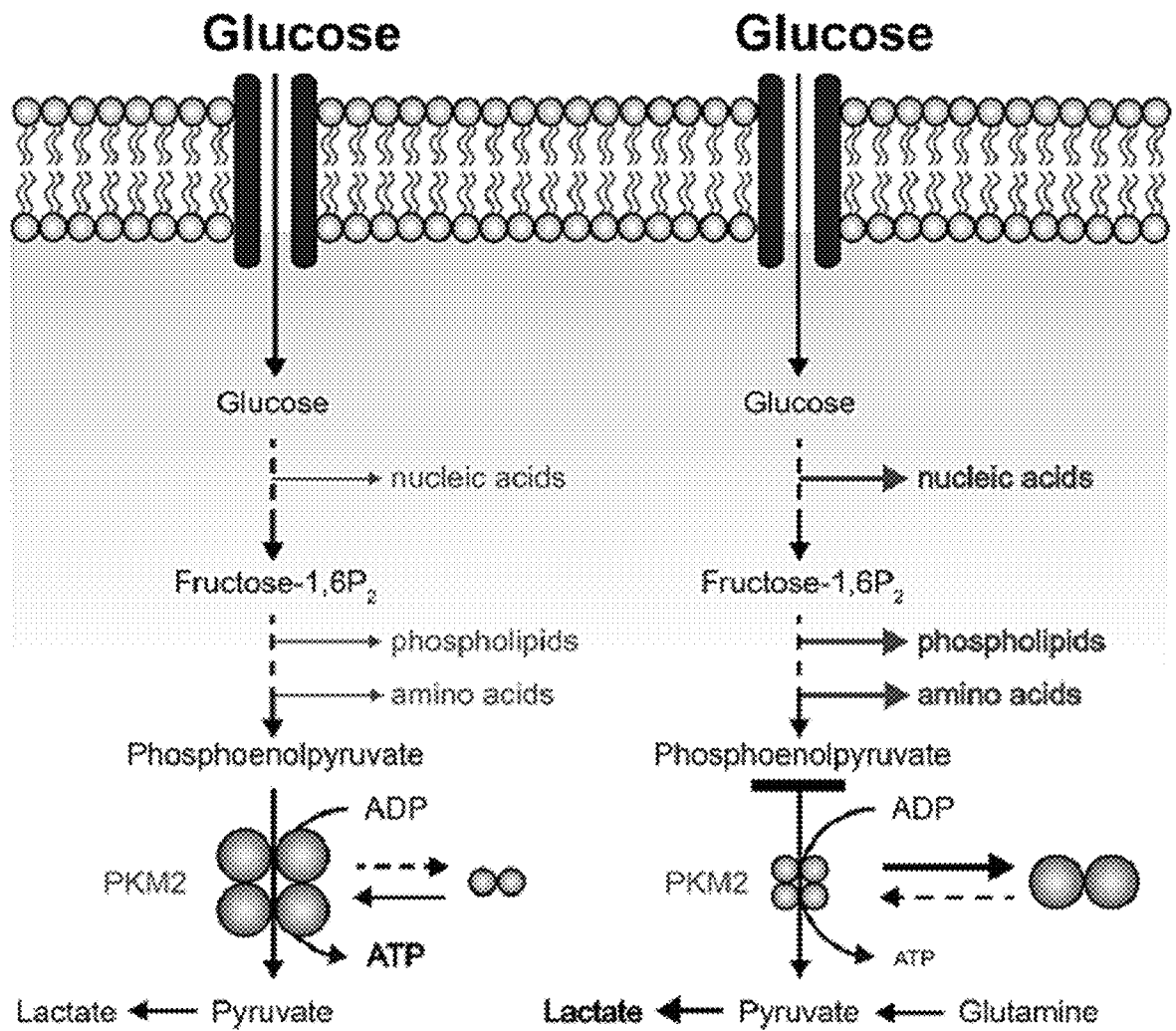
FIGS. 1A and 1B schematically illustrate the control of non-malignant and tumor glycolysis by pyruvate kinase M2 (PKM2).

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law, allowing for the presence of more than that which is recited so long as basic or novel characteristics of that which is recited is not changed by the presence of more than that which is recited, but excludes prior art embodiments.

Definitions

In describing and claiming the disclosed subject matter, the following terminology will be used in accordance with the definitions set forth below.

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art. As appropriate, procedures involving the use of commercially available kits and reagents are generally carried out in accordance with manufacturer defined protocols and/or parameters unless otherwise noted.

The term "cancer," as used herein, shall be given its ordinary meaning and is a general term for diseases in which abnormal cells divide without control. Cancer cells can invade nearby tissues and can spread through the bloodstream and lymphatic system to other parts of the body. There are several main types of cancer, for example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue, such as the bone marrow, and causes large numbers of abnormal blood cells to be produced and enter the bloodstream. Lymphoma is cancer that begins in the cells of the immune system.

When normal cells lose their ability to behave as a specified, controlled and coordinated unit, a tumor is formed. Generally, a solid tumor is an abnormal mass of tissue that usually does not contain cysts or liquid areas (some brain tumors do have cysts and central necrotic areas filled with liquid). A single tumor may even have different populations of cells within it with differing processes that have gone awry. Solid tumors may be benign (not cancerous) or malignant (cancerous). Different types of solid tumors are named for the type of cells that form them. Examples of solid tumors are sarcomas, carcinomas, and lymphomas. Leukemias (cancers of the blood) generally do not form solid tumors. Representative cancers include, but are not limited to, bladder cancer, breast cancer, colorectal cancer, endometrial cancer, head and neck cancer, leukemia, lung cancer, lymphoma, melanoma, non-small-cell lung cancer, ovarian cancer, prostate cancer, testicular cancer, uterine cancer, and cervical cancer.

A tumor can be classified as malignant or benign. In both cases, there is an abnormal aggregation and proliferation of cells. In the case of a malignant tumor, these cells behave more aggressively, acquiring properties of increased invasiveness. Ultimately, the tumor cells may even gain the ability to break away from the microscopic environment in which they originated, spread to another area of the body (with a very different environment, not normally conducive to their growth), and continue their rapid growth and division in this new location. This is called metastasis. Once malignant cells have metastasized, achieving a cure is more difficult.

Benign tumors have less of a tendency to invade and are less likely to metastasize. Brain tumors spread extensively within the brain but do not usually metastasize outside the brain.

Gliomas are very invasive inside the brain, even crossing hemispheres. They divide in an uncontrolled manner and, depending on their location, they can be as life threatening as other types of malignant lesions. For example, a glioma can grow and occupy space within the skull, leading to increased pressure on the brain.

The term "cell or population of cells" as used herein refers to an isolated cell or plurality of cells excised from a tissue or grown in vitro by tissue culture techniques. In the alternative, a population of cells may also be a plurality of cells in vivo in a tissue of an animal or human host.

The term "contacting a cell or population of cells" as used herein refers to delivering a composition such as, for example, a probe composition according to the present disclosure with or without a pharmaceutically or physiologically acceptable carrier to an isolated or cultured cell or population of cells, or administering the probe in a suitable pharmaceutically acceptable carrier to an animal or human host. Thereupon, it may be systemically delivered to the target and other tissues of the host, or delivered to a localized target area of the host. Administration may be, but is not limited to, intravenous delivery, intraperitoneal delivery, intramuscularly, subcutaneously or by any other method known in the art. One method is to deliver the composition directly into a blood vessel leading immediately into a target organ or tissue such as a prostate, thereby reducing dilution of the probe in the general circulatory system. It is contemplated that in the methods of the disclosure, administration or delivering a probe to an animal or human subject will result in the probe contacting a cell or population of cells (most advantageously a cancer cell or population of cancer cells). The probe may then enter the cell by active or passive transport.

The term "pharmaceutically acceptable carrier" as used herein refers to a diluent, adjuvant, excipient, or vehicle with which a probe of the disclosure is administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. When administered to a patient, the probes of the disclosure and pharmaceutically acceptable carriers preferably should be sterile. Water is a useful carrier when the probe of the disclosure is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use.

The term "positron emission tomography" as used herein refers to a nuclear medicine imaging technique that produces a three-dimensional image or map of functional processes in the body. The system detects pairs of gamma rays emitted indirectly by a positron-emitting radioisotope, which is introduced into the body on a metabolically active molecule. Images of metabolic activity in space are then reconstructed by computer analysis. Using statistics collected from tens-of-thousands of coincidence events, a set of simultaneous equations for the total activity of each parcel of tissue can be solved by a number of techniques, and a map of radioactivities as a function of location for parcels or bits of tissue may be constructed and plotted. The resulting map shows the tissues in which the molecular probe has become concentrated. Radioisotopes used in PET scanning are typically isotopes with short half-lives such as carbon-11 ($^{11}$C) (about 20 min), nitrogen-13 ($^{13}$N) (about 10 min), oxygen-15 ($^{15}$O) (about 2 min), and fluorine-18 ($^{18}$F) (about 110 min). PET technology can be used to trace the biologic pathway of any compound in living humans (and many other species as well), provided it can be radiolabeled with a PET isotope. The half-life of fluorine-18 ($^{18}$F) is long enough such that fluorine-18 labeled radiotracers can be manufactured commercially at an offsite location.

The term "label" as used herein refers to any moiety that may be linked (e.g. bonded or otherwise associated with) to the compounds of the present disclosure and which may be used to provide a detectable image including PET agents such as, but not limited to, $^{11}$C, $^{18}$F, $^{124}$I and $^{64}$Cu; or SPECT agents such as, $^{123}$I, $^{125}$I, or $^{131}$I.

The term "in vivo imaging" as used herein refers to methods or processes in which the structural, functional, or physiological state of a living being is examinable without the need for a life-ending sacrifice.

The term "non-invasive in vivo imaging" as used herein refers to methods or processes in which the structural, functional, molecular, or physiological state of being is examinable by remote physical probing without the need for breaching the physical integrity of the outer (skin) or inner (accessible orifices) surfaces of the body.

The term "alkoxy" as used herein refers to a linear or branched oxy-containing group having an alkyl portion of one to about ten carbon atoms, such as a methoxy group, which may be substituted. In aspects of the disclosure an alkoxy group may comprise about 1-10, 1-8, 1-6 or 1-3 carbon atoms. In embodiments of the disclosure, an alkoxy group comprises about 1-6 carbon atoms and includes a $C_1$-$C_6$ alkyl-O-group wherein $C_1$-$C_6$ alkyl has the meaning set out herein. Examples of alkoxy groups include without limitation methoxy, ethoxy, propoxy, butoxy, isopropoxy and tert-butoxy alkyls. An "alkoxy" group may, optionally, be substituted with one or more substitutents disclosed herein including alkyl atoms to provide "alkylalkoxy" groups, halo atoms, such as fluoro, chloro or bromo, to provide "haloalkoxy" groups (e.g. fluoromethoxy, chloromethoxy, trifluoromethoxy, difluoromethoxy, trifluoroethoxy, fluoroethoxy, tetrafluoroethoxy, pentafluoroethoxy, and fluoropropox), and "haloalkoxyalkyl" groups (e.g. fluoromethoxymethyl, chloromethoxyethyl, trifluoromethoxymethyl, difluoromethoxyethyl, and trifluoroethoxymethyl).

The term "substituted aryl" as used herein includes an aromatic ring or a fused aromatic ring system consisting of no more than three fused rings at least one of which is aromatic, and where at least one of the hydrogen atoms on a ring carbon has been replaced by a halogen, an amino, a hydroxy, a nitro, a thio, an alkyl, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, aminophenyl, hydroxyphenyl, chlorphenyl, and the like.

The term "pyruvate kinase" as used herein refers to an enzyme that catalyzes the transfer of a phosphoryl group from phosphoenolpyruvate (PEP) to ADP, yielding one molecule of pyruvate and one molecule of ATP. The enzyme has an absolute requirement for $Mg^{2+}$ and $K^+$ cations to drive catalysis. PK functions as the last critical step in glycolysis because it is an essentially irreversible reaction under physiological conditions. In addition to its role of synthesizing one of the two ATP molecules from the metabolism of glucose to pyruvate, pyruvate kinase is also an important cellular metabolism regulator. It controls the carbon flux in lower-glycolysis to provide key metabolite intermediates to feed biosynthetic processes, such as pentose-phosphate pathway among others, in maintaining healthy cellular metabolism. Because of these critical functions, pyruvate kinase is tightly controlled at both gene expression and enzymatic allostere levels. In mammals, fully activated pyruvate kinase exists as a tetrameric enzyme. Four different isozymes (M1, M2, L and R) are expressed from two separate genes. The mammalian isozymes PKM1 and PKM2 are produced from the PKM gene ("M gene") by alternative splicing events controlled by hnRNP proteins. The PKM2 isozyme is expressed in fetal tissues and in adult proliferating cells such as cancer cells.

Cancer cells rely primarily on glycolysis to generate cellular energy and biochemical intermediates for biosynthesis of lipids and nucleotides, while the majority of "normal" cells in adult tissues utilize aerobic respiration. This fundamental difference in cellular metabolism between cancer cells and normal cells, termed the Warburg Effect, has been exploited for diagnostic purposes but has not yet been exploited for therapeutic benefit. All tumor cells exclusively express the embryonic M2 isoform. A well-known difference between the M1 and M2 isoforms of PK is that M2 is a low-activity enzyme that relies on allosteric activation by the upstream glycolytic intermediate, fructose-1,6-bisphosphate (FBP), whereas M1 is a constitutively active enzyme.

PKM2 is also expressed in adipose tissue and activated T-cells. Phosphotyrosine peptide binding to PKM2 leads to a dissociation of FBP from PKM2 and conformational changes of PKM2 from an active, tetrameric form to an inactive form. Compounds that bind to PKM2 and lock the enzyme in the active confirmation will lead to the loss of allosteric control of PKM2 needed for shunting biochemical intermediates from glycolysis into biosynthesis of nucleotides and lipids. Thus, the activation of PKM2 can inhibit the growth and proliferation of cancer cells, activated immune cells, and fat cells. Activation of PKM2 may be effective in the treatment of cancer, obesity, diabetes, autoimmune conditions, and proliferation-dependent diseases, e.g., benign prostatic hyperplasia (BPH).

The term "activator" as used herein means an agent that (measurably) increases the activity of a pyruvate kinase (e.g., PKM2) or causes pyruvate kinase (e.g., PKM2) activity to increase to a level that is greater than PKM2's basal levels of activity. For example, the activator may mimic the effect caused by a natural ligand (e.g., FBP). The activator effect caused by the agent may be to the same, or to a greater, or to a lesser extent than the activating effect caused by a natural ligand, but the same type of effect is caused. Small molecules may be activators. An agent can be evaluated to determine if it is an activator by measuring either directly or indirectly the activity of the pyruvate kinase when subjected to the agent. The activity of the agent can be measured, for example, against a control substance. In some instances, the activity measured of the agent is for activation of PKM2. The activity of PKM2 can be measured, for example, by monitoring the concentration of a substrate such as ATP or NADH.

Further definitions are provided in context below. Unless otherwise defined, all technical and scientific terms used herein have the same meaning as commonly understood by one of ordinary skill in the art of molecular biology. Although methods and materials similar or equivalent to those described herein can be used in the practice or testing of the present disclosure, suitable methods and materials are described herein.

Abbreviations

PET, Positron Emission Tomography; MRI, Magnetic Resonance Imaging; PK, pyruvate kinase; PKM2, splice variant of pyruvate kinase; PEP, phosphoenylpyruvate; DASA, N,N-diarylsulfonamide; TEPP-46, 6-(3-Aminophenyl)methyl)-4-methyl-2-methylsulfinylthieno[3,4]pyrrolo [1,3-d]pyridazin-5-one; i.p.: intraperitioneal; s.c.: subcutaneous; i.v.: intravenous; FBP, fructose 1,6 biphosphate.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art, are hereby incorporated by reference.

Discussion

Figure 1B:
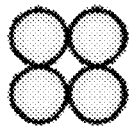
Figure 1B:
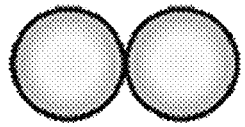

Pyruvate Kinase: Pyruvate kinase (PK) catalyzes the final and rate-limiting reaction in glycolysis, converting phosphoenolpyruvate (PEP) to pyruvate by transferring the high-energy phosphate group to ADP to produce ATP. PK consists of four isoforms, of which the spliced variant, PKM2, is preferentially expressed in all cancers studied to-date, regardless of their tissue of origin (Wong et al., (2013) *Int. J. Cell Biol.* 2013: 242513). PKM2 is allosterically regulated by the stabilization of a highly active tetramer relative to monomeric/dimeric PKM2. The tetramer of PKM2 has a high affinity for PEP, favoring synthesis of ATP and pyruvate, whereas the monomer/dimer has reduced activity because of its low affinity for PEP at physiological concentrations (Dombrauckas et al., (2005) *Biochemistry* 44: 9417-9429). When PKM2 is in the monomeric/dimeric conformation, reduced glycolytic flux through to pyruvate results in the accumulation of precursors for the biosynthesis of amino acids, nucleic acids, and phospholipids, commensurate with the production of reducing power through pentose phosphate pathway-derived NADPH (Mazurek S. (2011) *Int. J. Biochem. Cell Biol.* 43: 969-980). A dynamic equilibrium between the two states of PKM2 enables tumor cells to switch between anabolic and catabolic metabolism, as shown in FIG. 1A. Alternative splicing of PKM2 is controlled by c-Myc and HIF-1 oncogenes (Chaneton & Gottlieb (2012) *Trends Biochem. Sci.* 37: 309-316), with quaternary structure of PKM2 tightly regulated by the glycolytic intermediate fructose 1,6-bisphosphate (FBP) (Bailey et al., (1968) *Biochem J.* 108: 427-436) and growth factor signaling (Christofk et al., (2008) *Nature* 452: 181-186), as shown in FIG. 1B. In recent years, PKM2 has been targeted for cancer therapy through the development of small molecule activators that promote tetramer formation (Boxer et al., (2010) *J. Med. Chem.* 53: 1048-1055; Israelsen et al., (2013) *Cell* 155: 397-409).

Tumor cells reprogram their metabolism in response to the increased anabolic and catabolic demands of highly-proliferative cells. For many metabolic pathways, the balance between biomolecular synthesis and energy production is highly regulated. An elegant example is provided in the case of acetyl CoA carboxylase, which controls the opposing rates of fatty acid synthesis and oxidation on the basis of intracellular concentrations of acetyl CoA and malonyl CoA (Tong L. (2005) *Cell. Mol. Life Sci.* 62: 1784-1803). Altered tumor glycolysis is mediated, in part, by PKM2 through transcriptional and epigenetic means (David et al., (2010) *Nature* 463: 364-U114; Luo et al. (2011) *Cell* 145: 732-744; Lv et al. (2011) *Mol. Cell* 42: 719-730), with a growing body of evidence demonstrating a critical role of PKM2 in tumorigenesis and progression (Wong et al., (2013) *Int. J. Cell Biol.* 2013: 242513). Further evidence suggests that PKM2 might provide a similar regulatory switch to acetyl CoA carboxylase; controlling the balance between glycolytically-derived anabolic and catabolic metabolism (Mazurek S. (2011) *Int. J. Biochem. Cell Biol.* 43: 969-980; Christofk et al., (2008) *Nature* 452: 181-186; Eigenbrodt et al., (1992) *Critical Revs Oncogenesis* 3: 91-115; Vander Heiden et al., (2009) *Science* 324: 1029-1033). PKM2 has additionally been shown to translocate to the nucleus where it functions to promote cell proliferation through interaction with HIF, STAT 3, Oct 4 and β-catenin (reviewed in Chaneton & Gottlieb (2012) *Trends Biochem. Sci.* 37: 309-316).

Although of great interest and importance, non-invasive imaging of PKM2 with clinically-relevant probes and imaging modalities has not yet been reported. PKM2 is overexpressed in tumors (Wong et al., (2013) *Int. J. Cell Biol.* 2013: 242513) and expressed in most tissues to varying degrees, with the exception of adult muscle, brain and liver (Bluemlein et al. (2011) *Oncotarget* 2: 393-400; Christofk et al. (2008) *Nature* 452: 230-233; Imamura & Tanaka (1972) *J. Biochem.* 71: 1043-1051).

Given the importance of PKM2 in the regulation of tumor metabolism, there is an on-going need to non-invasively measure its expression through the development of PKM2-specific radiopharmaceuticals. A class of N,N-diarylsulfonamides (DASA) was reported by Boxer et al. in 2010 as PKM2 activators (Boxer et al., (2010) *J. Med. Chem.* 53: 1048-1055), known to promote PKM2 tetramer formation through binding at the subunit interaction interface of the PKM2 dimer in an allosteric pocket that is distinct from the binding site of fructose 1,6-bisphosphate, thereby inhibiting tumor growth in vivo (Anastasiou et al., (2012) *Nat. Chem. Biol.* 8: 839-847). The disclosure provides embodiments of precursors useful for the synthesis of novel positron emission tomography (PET) radiotracers for the detection of the dimeric PKM2, radiolabeled [$^{18}$F]DASA-23-PKM2-specific probes and related compounds, and their methods of synthesis. Accordingly, the ability of [$^{18}$F]DASA-23 probe and analogs thereof are advantageous for the detection of tumor-specific PKM2 in subcutaneous and orthotopic mouse models of human glioma in vivo.

The present disclosure, therefore, provides PET-detectable probes that can selectively bind to the pyruvate kinase variant M2 (PKM2) that is found in cancer cells. It is further contemplated that the probes of the disclosure can be advantageously used to detect PKM2 expression in cells other than just cancer cells. In the embodiments of the radiolabeled probes of the disclosure, the radionuclide conjugated thereto is advantageously the isotope $^{18}$F. Most advantageously, the present disclosure encompasses the addition of at least one $^{18}$F moiety onto a phenyl ring of the PKM2 activator.

There is no clinically approved PET tracer that can be specifically used to visualize PKM2 expression. The PET tracer [1-((2,6-difluorophenyl) sulfon-yl)-4-(4-([11C]) methoxyphenyl)sulfonyl)piperazine] ([$^{11}$C]DASA-23) (Witney et al., (2015) Sci. Transl. Med. 7: 310ra169) was developed to meet this need, and it was demonstrated that [$^{11}$C]DASA-23 could detect tumor-specific PKM2 in subcutaneous and orthotopic mouse models of human glioma in vivo. These findings provided a foundation for the clinical translation of [$^{11}$C]DASA-23 for the imaging of primary brain tumors and other tumors that metastasize to the brain. However, the physical characteristics of C-11 limit its clinical utility and practicality. The relatively short half-life of C-11 ($t_{1/2}$=20.4 min) requires an on-site cyclotron within hospitals and imaging centers and consequently hinders the clinical application of this diagnostic radiotracer. The increasing clinical use of PET imaging and the limited availability of cyclotrons within clinical PET facilities have resulted in the development of numerous PET radiotracers labeled with F-18. The half-life of F-18 ($t_{1/2}$=110 min) potentially allows remote site synthesis which has been extensively demonstrated with the world-wide use and distribution of [$^{18}$F]FDG. The presence of fluorine atoms in the native structure of DASA-23, however, poses a challenge to introduce the F-18 label into its native position with nucleophilic fluorination. An advantage of radiolabelling at these native sites is that 1-((2-fluoro-6-(fluoro-$^{18}$F) phenyl) sulfonyl)-4-((4-methoxyphenyl)sulfonyl)piperazine ([$^{18}$F] DASA-23) will maintain the same binding characteristics and specificity towards PKM2 as [$^{11}$C]DASA-23.

The present disclosure encompasses novel synthetic procedures for radiolabeling the PKM2 activator DASA-23 by introducing the $^{18}$F label to the novel precursor 4-((4-((2-fluoro 6-nitrophenyl)sulfonyl)piperazin-1-yl)sulfonyl)phenol (I) (or such as 4-((4-((2,6-dinitrophenyl)sulfonyl)piperazin-1-yl)sulfonyl)phenol, itself generated by a novel synthetic pathway (Scheme A). Further, since the half-life of the $^{18}$F isotope is approximately 110 min, it is advantageous for a practitioner desirous of administering the probes of the disclosure to a patient for the purposes of generating a PET image thereof to attach the radionuclide to the precursor shortly before administration. It is contemplated, therefore, that a precursor compound suitable for receiving the radionuclide and capable of specifically binding to the PKM2 variant may be provided. Methods, therefore, are provided for the generation of such a precursor and the radiolabeling of such. Most advantageously, a suitable precursor can have the formula (I).

The present disclosure further demonstrates the advantage that the PKM2-specific radiolabeled probe can surprisingly traverse the blood-brain barrier and then allow imaging of cancer cells such as gliomal cells in the brain. Accordingly, the probes of the disclosure allow methods of acquiring images, and in particular PET images, of tumors in the brain, in the prostate, and in other tissues.

Figure 4:
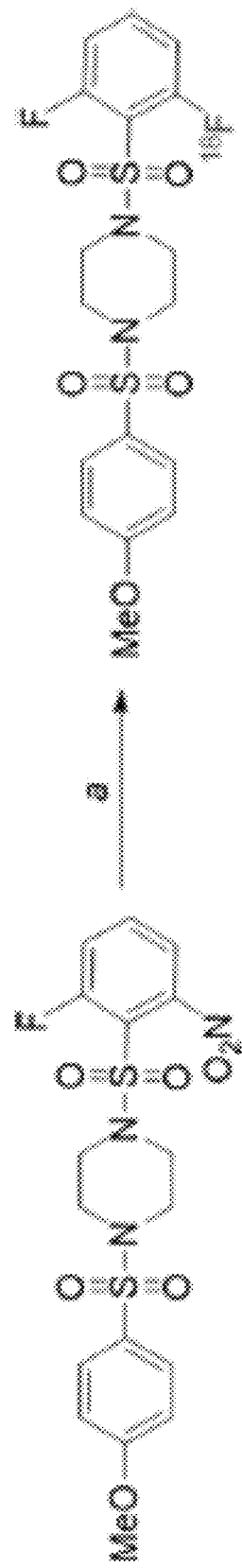
FIG. 4 illustrates scheme 3 for the synthesis of [$^{18}$F] DASA-23. Reagents and conditions. a [$^{18}$F]KF/K2.2.2, DMF, 110° C., 20 min, 2.61±1.55% nondecay corrected at EOS (n=10).

Given the intrinsically low background of PKM2 in the brain, it was considered whether PKM2 is up-regulated in transformed human glioblastoma cells by using orthotopic mouse models of the disease, and whether it was possible to measure this transformation non-invasively through imaging. By using the $^{18}$F-labelled PKM2 activator $^{18}$F-DASA-23 (III), which displays selective activation of PKM2 (AC$_{50}$=90 nM) versus other pyruvate kinase isozymes, PKM1, PKR and PKL (Boxer et al., (2010) J. Med. Chem. 53: 1048-1055), high tumor cell uptake of the tracer in culture is now demonstrated, with uptake strongly correlated to PKM2 protein expression. As DASA-23 reversibly binds to PKM2, efflux of the tracer from tumor cells following removal of exogenous activity is expected, although this occurs at a relatively slow rate. Of note is the ability of [$^{18}$F]DASA-23 probes of the disclosure to measure increased PKM2 expression following prolonged incubation in media (up to 72 h; FIG. 4). Cell adaptation to a reduced nutrient environment, akin to poorly perfused tumors in vivo, hints at an important role for PKM2 in the maintenance of metabolic homeostasis. PKM2 is degraded when glucose is abundant via acetylation and chaperone-mediated autophagy, a process which is inhibited under nutrient stress (Lv et al., (2011) Mol. Cell 42: 719-730). The ability to detect these chronically nutrient-deprived cells, through PKM2 imaging, may provide novel insights into tumor progression and metastasis, given that these cells are relatively chemoresistant (Gatenby & Gillies (2004) Nature Revs. Cancer 4: 891-899).

Figure 2:
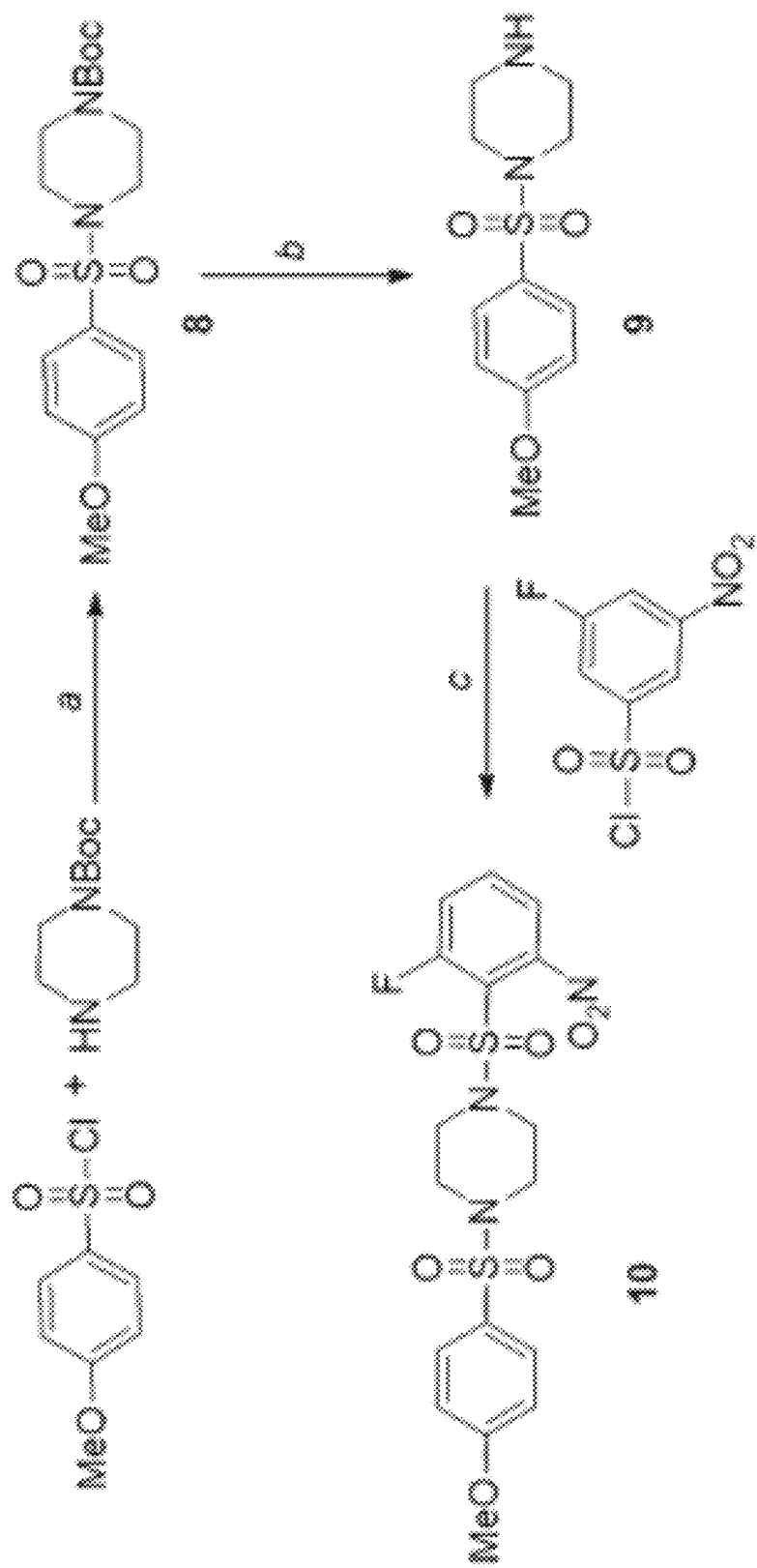
FIG. 2 illustrates scheme 1 for the synthesis of nitro precursor 10. Reagents and conditions. a $NEt_3$, $CH_2Cl_2$, 0° C., 1 h, 42%. b TFA, $CH_2Cl_2$, 0° C., 1 h. c $NEt_3$, $CH_2Cl_2$, 0° C., 1 h, 85%.

Given the good in vitro uptake profile and relatively high lipophilicity (c Log P=3.4, ChemDraw Bio 13.0) of [$^{18}$F] DASA-23 (required for diffusion across the blood brain barrier), [$^{18}$F]DASA-23 was examined for suitability for use in pre-clinical in vivo imaging of a human glioma. The combined renal and hepatobiliary excretion profile for [$^{18}$F] DASA-23 (FIGS. 2 and 5), however, indicates that this probe is advantageous for the imaging of PKM2 to tumors of the brain after rapid initial uptake and washout and of the upper thoracic region. Tumor-to-muscle and blood background ratios, although statistically significant, were below those typically observed with FDG-PET (Witney et al., (2015) Clin. Cancer Res. 21: 3896-3905).

High-quality PET/CT images (FIG. 2) were obtained. Low background radioactivity was detected in normal tissue of the brain, as predicted by the absence of PKM2 expression previously measured in this tissue (Imamura & Tanaka (1972) J. Biochem. 71: 1043-1051).

The increased glucose utilization of tumors in comparison to normal tissue (the "Warburg effect") has previously been exploited clinically to detect tumors and their response to treatment by [$^{18}$F]2-fluoro-2-deoxy-D-glucose ([$^{18}$F]FDG) PET. $^{18}$F-FDG-PET is approved for use for the diagnosis of the majority of cancers (Kelloff et al., (2005) Clin. Cancer Res. 11: 2785-2808), with particular utility for detecting metastases and nodal disease that appear normal on x-ray computed tomography scans (Sharma et al., (2004) Radiological Soc. North Am. 24: 419-434). Some tumors however are not [$^{18}$F]FDG-avid, e.g., prostate adenocarcinoma (Takahashi et al., (2007) Oncology 72: 226-233), whereas a high background uptake by surrounding normal tissue can mask tumor uptake, for example, in the brain (Phelps & Mazziotta (1985) Science 228: 799-809).

Accordingly, [$^{18}$F]DASA-23 is useful for the non-invasive measurement of malignancies where FDG has failed. Several other radiotracers, such as 3,4-dihydroxy-6-[$^{18}$F] fluoro-phenylalanine ([$^{18}$F-FDOPA) (Karunanithi et al., (2013) *Eur. J. Nucl. Med. Mol. Imaging* 40: 1025-1035), O-(2-[$^{18}$F]fluoroethyl)-L-tyrosine (FET) (Weber et al., (2000) *Eur. J. Nucl. Med.* 27: 542-549), 4-[$^{18}$F]-(2S,4R)-fluoroglutamine (Venneti et al., (2015) *Sci. Transl. Med.* 7: 274ra217, and (4S)-4-(3-[$^{18}$F]fluoropropyl)-L-glutamate ([$^{18}$F]FSPG) (Baek et al., (2012) *Clin. Cancer Res.* 18: 5427-5437) have shown great value for imaging tumors of the brain. In contrast, the present disclosure encompasses probes directed to non-invasive measurement of PKM2 status in these tumors.

Regarding diagnostic utility, therefore, [$^{18}$F]DASA-23 can be advantageously employed in the non-invasive measurement of malignancies where FDG fails. Given the great interest in targeting PKM2 for cancer therapy (Boxer et al., (2010) *J. Med. Chem.* 53: 1048-1055; Anastasiou et al., (2012) *Nature Chem. Biol.* 8: 839-847; Vander Heiden et al., (2010) *Biochem. Pharmacol.* 79: 1118-1124; Walsh et al., (2011) *Bioorganic Med. Chem. Letts.* 21: 6322-6327), [$^{11}$C] DASA-23 and the derivatives thereof as described in the present disclosure, may also provide a means to measure the therapeutic efficacy of these novel agents.

Accordingly, a PKM2-binding PET radiotracer family has been developed that enables the specific and sensitive pre-clinical detection of orthotopically-growing human glioblastoma. This study sets the foundation for the clinical translation of [$^{18}$F]DASA-23 for the imaging of primary and metastatic gliomas. [$^{18}$F]DASA-23 PET and derivatives thereof can be useful as a companion diagnostic and for the assessment of tumor aggressiveness. DASA-23 was labeled here with $^{11}$C to preserve the compound's specificity and selectivity for PKM2 binding (Boxer et al., (2010) *J. Med. Chem.* 53: 1048-1055).

The present disclosure describes the synthesis and radio-labelling of [$^{18}$F]DASA-23, a PKM2 activator from the N—N'-diarylsulfonamide class of ligands, combined with its in vitro characterization using cell uptake and stability studies.

DASA-23 is advantageous for radiolabelling due to its potency as a PKM2 activator, with a maximum activating concentration (AC$_{50}$) of 90 nM and also its selectivity for PKM2 relative to other PK enzymes, PKM1, PKR, and PKL (Boxer et al., (2010) *J. Med. Chem.* 53: 1048-1055). This class of PKM2 activator has been described to activate the PKM2 isoform by reducing the K$_m$ (Michaelis constant) for PEP while conserving the affinity of PKM2 for ADP (Boxer et al., (2010) *J. Med. Chem.* 53: 1048-1055). PKM2 activators are known to bind a pocket at the PKM2 subunit interface which promotes association of PKM2 subunits into stable tetramers (Anastasiou et al., (2012) *Nat. Chem. Biol.* 8: 839-847). Structural analyses of activators bound to PKM2 tetramers have revealed a binding pocket present at the interface of the subunit interaction, which was distinct from the FBP binding site. Small molecular activators were found to stabilize the A-A' interface of the active tetramer, unlike FBP which stabilizes the C-C' interface (Anastasiou et al., (2012) *Nat. Chem. Biol.* 8: 839-847). No natural ligands have been identified for this binding site of PKM2, considering that multiple classes of activators bind this pocket; it is possible that this signifies a novel site of pyruvate kinase regulation.

It was found that [$^{11}$C]DASA-23 successfully detected orthotopically growing human glioblastoma with aberrantly expressed PKM2 in mouse models. The intrinsically low background of PKM2 in the healthy brain also provided an optimal signal-to-background ratio (Witney et al., (2015) *Sci. Transl. Med.* 7: 310ra169). The in vivo specificity of [$^{11}$C]DASA-23 for PKM2 was demonstrated through competition studies with structurally distinct PKM2 activator, TEPP-46 (Witney et al., (2015) *Sci. Transl. Med.* 7: 310ra169). This work sets the foundation for clinical translation of [$^{11}$C]DASA-23 for the imaging of primary brain tumors and potentially other tumors that metastasize to the brain. The favorable physical characteristics of fluorine-18 ($t_{1/2}$=110 min) relative to carbon-11 ($t_{1/2}$=20.4 min) and the presence of fluorine atoms in the native structure of DASA-23 allowed the advantageous introduction of the F-18 label into the native position to facilitate clinical translation of this radiotracer. Labelling DASA-23 with F-18 in the native site on the molecule will not alter in any way the compound structure and therefore already established binding to PKM2.

Radiolabelling of DASA-23 was achieved by fluorine-18 nucleophilic displacement of the aryl nitro moiety within compound 10. The nucleophilic displacement by fluorine-18 of a nitro group activated by electron-withdrawing groups is a well-established and efficient method for the preparation of carrier-free F-18-labeled aromatics (Attina et al., (1983) *J. Chem. Soc. Chem. Commun.* 1983: 108-109; Attiná et al., (1983) *J. Labelled Comp. Radiopharm.* 20: 501-514; Plenevaux et al., (1992) *Int. J. Rad. Appl. Instrum.* 43: 1035-1040). This methodology has been widely applied to the preparation of radio pharmaceuticals (a notable example being [$^{18}$F]spiroperidol) and for the preparation of synthetically-useful labeled intermediates (Attiná et al., (1983) *J. Labelled Comp. Radiopharm.* 20: 501-514).

Radiolabelling of DASA-23 was achieved by heating the fluorination reaction at 110° C. for 20 min (precursor concentration 300 µg/ml); this afforded high purity product in sufficient yields (2.61±1.54%) for preliminary in vitro characterization. Since heating the reaction at 110° C. for 20 min afforded high purity product in sufficient yields for preliminary in vitro evaluation, no further optimizations were pursued at this stage. Evaluation of the tracer in HeLa cells showed that [$^{18}$F]DASA-23 exhibited rapid and high levels of uptake and retention. Rapid uptake is necessary for [$^{18}$F]DASA-23, with a half-life of 110 min, to be an effective PET tracer. The specificity of this tracer for PKM2 was confirmed by co-incubating cells with [$^{18}$F]DASA-23 and TEPP-46. TEPP-46 is a structurally distinct PKM2 activator (AC$_{50}$=92 nM) known to bind the same allosteric pocket as DASA-23, therefore blocking the PKM2 activator binding. This resulted in significant blocking of tracer uptake, therefore indicating that the tracer is specific and may be a suitable marker of PKM2 expression levels. In vitro stability studies revealed that [$^{18}$F]DASA-23 is stable in both human and mouse serum up to 120 min. This suggests that [$^{18}$F] DASA-23 may be transported to tissues in its intact form. Taken together, these data indicate that [$^{18}$F]DASA-23 is advantageous as a specific radiotracer for the precise identification and visualization of PKM2 expression.

The present disclosure provides, therefore, a novel synthetic procedure towards DASA-23 that incorporates a nitro-containing precursor (FIG. 2) to be used for radiolabelling with fluorine-18. [$^{18}$F]DASA-23 can then be generated via fluorination of 1-((2-fluoro-6-nitrophenyl)sulfonyl)-4-((4-methoxyphenyl)sulfonyl)piperazine with K[$^{18}$F]F/K2.2.2 (FIG. 4). In an alternative embodiment of the synthetic procedure shown in FIG. 2, instead of using 2-fluoro-6-nitrobenzenesulfonyl chloride, it is contemplated that a 2-halogen-6-fluorobenzenesulfonyl chloride (such as 2-Bromo-6-fluorobenzenesulfonyl chloride) may be used to provide a halogen leaving group for subsequent fluorination.

Cell culture studies showed rapid cellular uptake of the tracer in HeLa tumor cells post addition of [$^{18}$F]DASA-23. Removal of tracer from the cell media resulted in some efflux of the cell-associated radioactivity, but over 50% of the tracer is still retained 30 min after removal of the [$^{18}$F]DASA-23 from media. Upon addition of TEPP-46, a structurally distinct class of PKM2 activator, significant blocking of tracer uptake was observed.

Figure 12A:
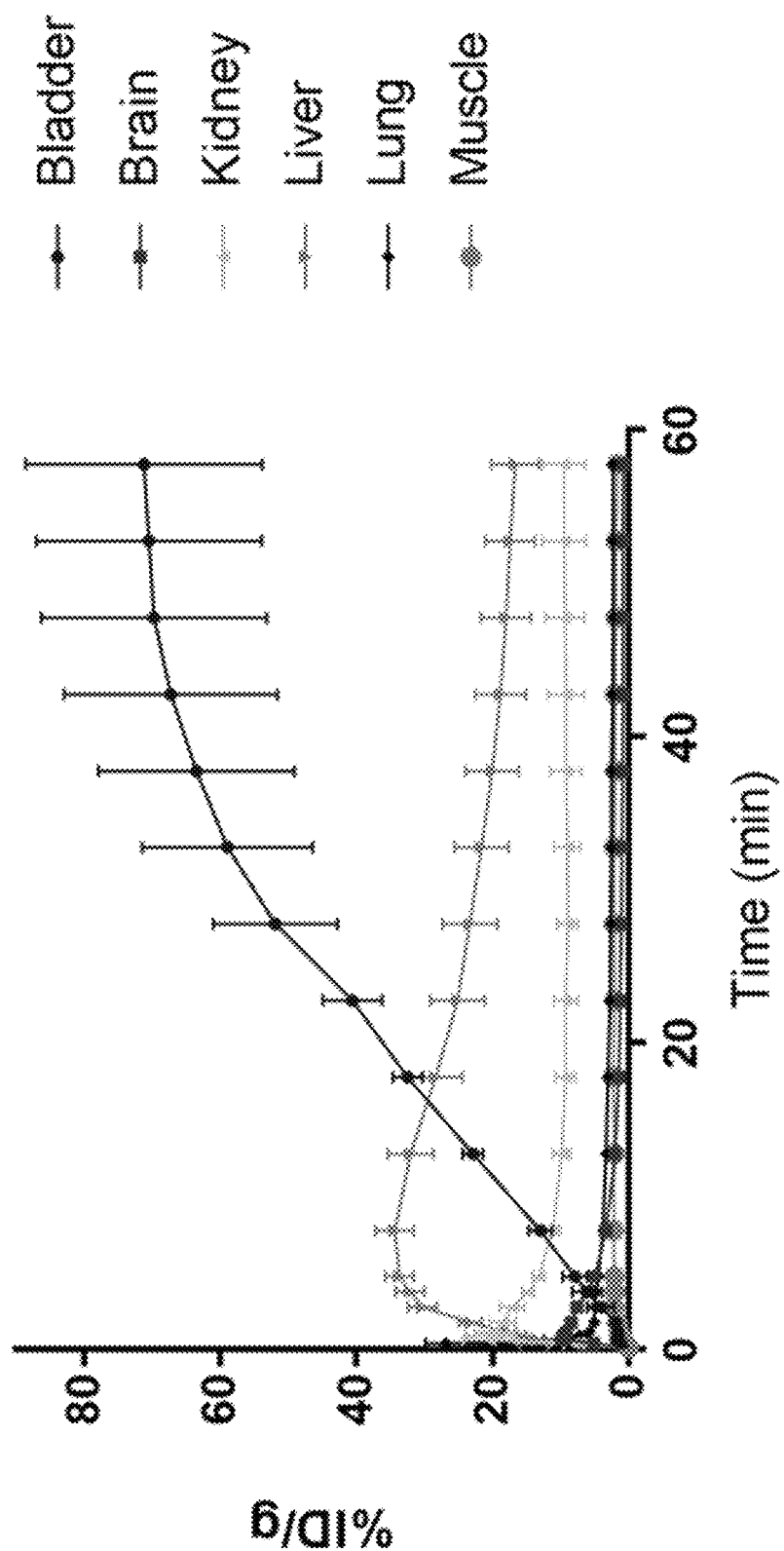
FIG. 12A is a time-activity graph illustrating the distribution of [$^{18}$F]DASA-23 in organs of mice.
Figure 12B:
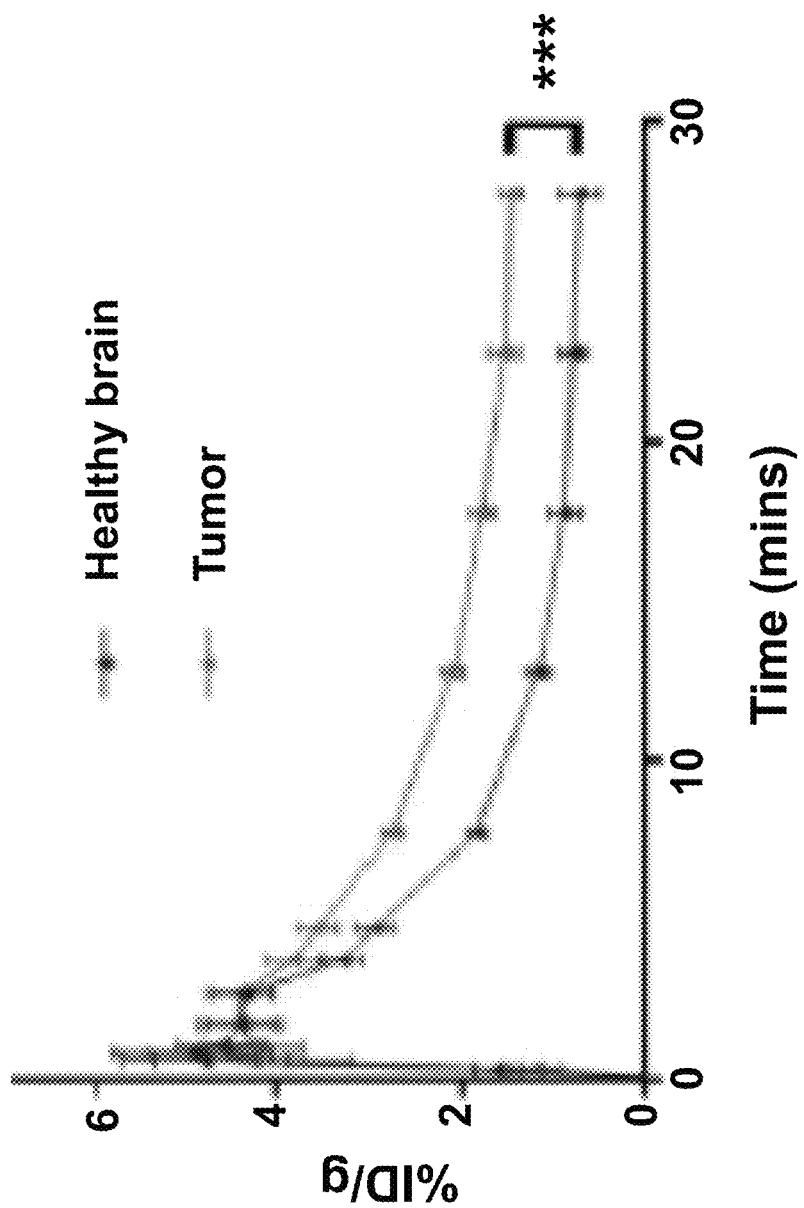
FIG. 12B illustrates non-invasive imaging of mice bearing orthotopic U87 tumor showing orthotopic U87 tumor and corresponding contralateral normal brain TAC taken from dynamic [$^{18}$F]DASA-23 PET/CT images. Data are means±SD (n=6 animals), ***$p<0.001$.
Figure 13:
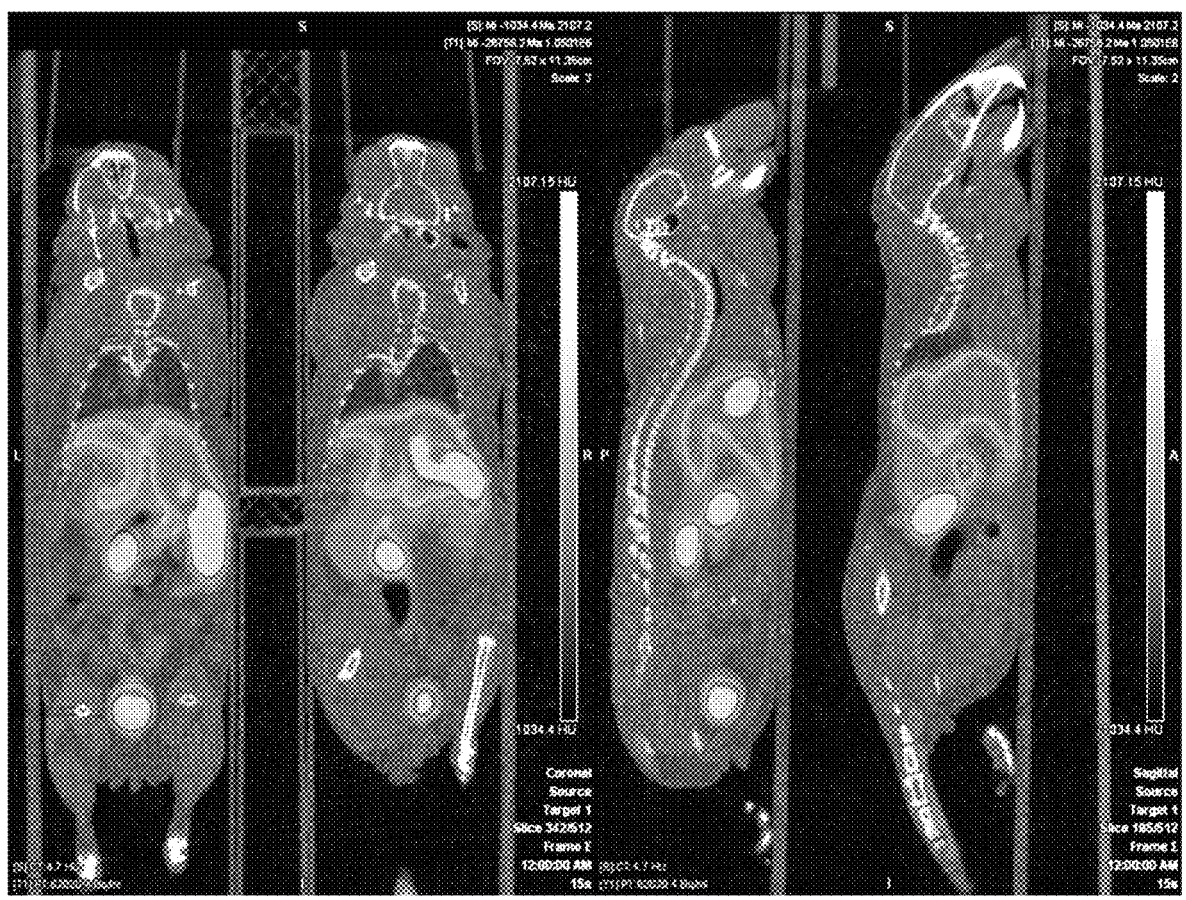
FIG. 13 illustrates the summed PET images 60 mins after injection of [$^{18}$F]DASA-23 into mice.

In vivo, orthotopic U87 GBM tumors could be clearly delineated from the surrounding normal brain tissue by dynamic PET imaging (n=6 mice; FIGS. 12A and 12B). PET/MR co-registration confirmed precise correspondence of the [$^{18}$F]DASA-23 signal with the location of the intracranial tumors, further confirmed ex vivo by autoradiography. The autoradiography results for selected coronal brain sections from both the baseline and blocking study (the latter of which was pre-treated with TEPP-46 prior to injection with [$^{18}$F]DASA-23) are shown in FIGS. 12A and 12B. It is evident that [$^{18}$F]DASA-23 accumulates in the tumor, with results from the blocking study clearly depicting a dramatic reduction in tumor uptake. These data highlight the specificity of [$^{18}$F]DASA-23 for PKM2 and indicate that signal in the tumor is the result of tracer binding at PKM2. Together, these data demonstrate that [$^{18}$F]DASA-23 successfully measures tumor-associated PKM2 in preclinical models of human GBM and provides the foundation for clinical translation of this imaging agent.

Accordingly, one aspect of the disclosure encompasses embodiments of a pyruvate kinase M2 activator precursor having the formula I:

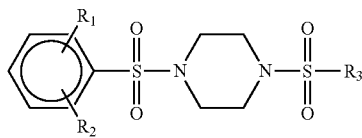

wherein at least one of $R_1$ and $R_2$ can be $NO_2$; when $R_2$ is $NO_2$, $R_1$ is F or $NO_2$; and $R_3$ is a substituted aryl, naphthalene, or 1,4 benzodioxane.

In some embodiments of this aspect of the disclosure, $R_3$ can be an alkoxyphenyl or an aminophenyl.

In some embodiments of this aspect of the disclosure, $R_3$ is 4-methoxyphenyl, 4-ethoxyphenyl, 4-propoxyphenyl, or 4-aminophenyl.

In some embodiments of this aspect of the disclosure, the precursor has the formula II:

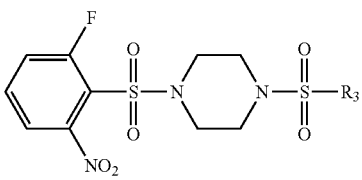

wherein $R_3$ is a substituted aryl.

In some embodiments of this aspect of the disclosure, $R_3$ is 4-methoxyphenyl.

Another aspect of the disclosure encompasses embodiments of a Positron Emission Tomography (PET)-detectable probe having the formula III:

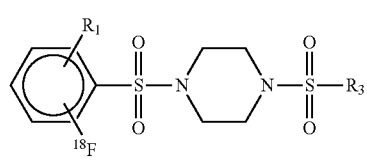

wherein $R_1$ is F or $^{18}$F; and $R_3$ can be a substituted aryl, naphthalene, or 1,4 benzodioxane.

In some embodiments of this aspect of the disclosure, $R_3$ is an alkoxyphenyl or an aminophenyl.

In some embodiments of this aspect of the disclosure, $R_3$ is 4-methoxyphenyl, 4-ethoxyphenyl, 4-propoxyphenyl, or 4-aminophenyl.

In some embodiments of this aspect of the disclosure, the probe has the formula IV:

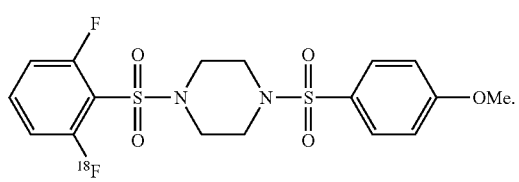

Still another aspect of the disclosure encompasses embodiments of a pharmaceutically acceptable probe composition comprising a Positron Emission Tomography (PET)-detectable radiolabelled probe having the formula III:

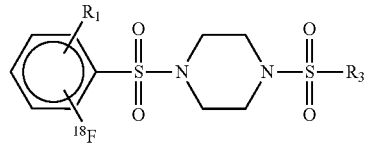

wherein $R_1$ is F or $^{18}$F; and $R_3$ can be a substituted aryl, naphthalene, or 1,4 benzodioxane.

In some embodiments of this aspect of the disclosure, the probe can have the formula IV:

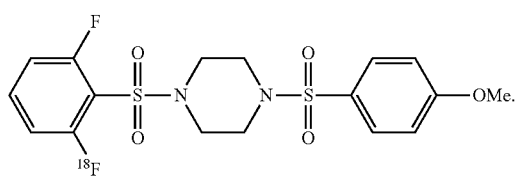

In some embodiments of this aspect of the disclosure, the pharmaceutically acceptable probe composition can further comprise a pharmaceutically acceptable carrier.

Still another aspect of the disclosure encompasses embodiments of a method of generating a pyruvate kinase M2 activator precursor, wherein said precursor is 1-((2- fluoro-6-nitrophenyl)sulfonyl)-4-((4-methoxyphenyl)sulfonyl)piperazine (10) having the formula II:

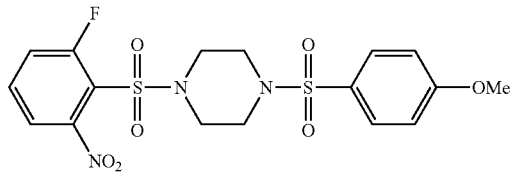

the method comprising the steps of: (a) reacting 1-Boc-piperazine, trimethylamine and 4-methoxybenzenesulfonyl chloride to generate tert-butyl 4-((4-methoxyphenyl)sulfonyl)piperazine-1-carboxylate (8); (b) quenching the reaction of step (a) with saturated aqueous ammonium chloride and purifying the first product; (c) reacting the product of step (b) with trifluoroacetic acid to generate a TFA salt of 1-((4-methoxyphenyl)sulfonyl)piperazine (9); and (d) reacting the TFA salt of 1-((4-methoxyphenyl)sulfonyl)piperazine (9) product of step (c) with 2-fluoro-6-nitrobenzenesulfonyl chloride to generate 1-((2-fluoro-6-nitrophenyl)sulfonyl)-4-((4-methoxyphenyl)sulfonyl)piperazine (10) or with 2-bromo-6-fluorobenzenesulfonyl chloride to generate 1-((2-bromo-6-fluorobenzenesulfonyl)-4-((4-methoxyphenyl)sulfonyl)piperazine In some embodiments of this aspect of the disclosure, the step (d) can comprise reacting the TFA salt of 1-((4-methoxyphenyl)sulfonyl)piperazine (9) product of step (c) with 2-fluoro-6-nitrobenzenesulfonyl chloride to generate 1-((2-fluoro-6-nitrophenyl)sulfonyl)-4-((4-methoxyphenyl)sulfonyl)piperazine (10).

Still another aspect of the disclosure encompasses embodiments of a method of generating a radiolabelled probe, wherein the probe is 1-((2-fluoro-6-(fluoro-$^{18}$F)phenyl)sulfonyl)-4-((4-methoxyphenyl)sulfonyl)piperazine, said method comprising the steps: (a) fluoridating 4,7,13,16,21,24-hexaoxa-1,10-diazabicyclo[8.8.8]hexacosan (K2.2.2) with $^{18}$F; and (b) reacting 1-((2-fluoro-6-nitrophenyl)sulfonyl)-4-((4-methoxyphenyl)sulfonyl)piperazine (10) or 1-((2-bromo-6-fluorobenzenesulfonyl)-4-((4-methoxyphenyl)sulfonyl)piperazine with the fluoridated product of step (a), thereby obtaining 1-((2-fluoro-6-(fluoro-$^{18}$F)phenyl)sulfonyl)-4-((4-methoxyphenyl)sulfonyl)piperazine.

In some embodiments of this aspect of the disclosure, the step (b) can comprise reacting 1-((2-fluoro-6-nitrophenyl)sulfonyl)-4-((4-methoxyphenyl)sulfonyl)piperazine (10) with the fluoridated product of step (a), thereby obtaining 1-(2-fluoro-6-(fluoro-$^{18}$F)phenyl)sulfonyl)-4-(4-methoxyphenyl)sulfonyl)piperazine.

Still another aspect of the disclosure encompasses embodiments of a method of detecting a cell or a population of cells expressing pyruvate kinase M2, said method comprising: (i) contacting a cell or population of cells with a pharmaceutically acceptable PET-detectable radiolabelled probe composition comprising at least one probe having a radionuclide and having the formula:

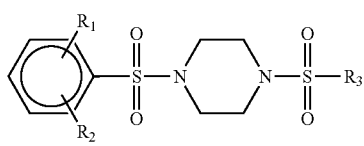

wherein $R_2$ is $^{18}$F and $R_1$ can be F or $^{18}$F; and $R_3$ can be a substituted aryl, naphthalene, or 1,4 benzodioxane; and (ii) detecting pyruvate kinase M2-specific binding of the radionuclide-containing probe within the cell or population of cells by detecting the presence of the radionuclide in the cell or population of cells.

In some embodiments of this aspect of the disclosure, the probe can have the formula IV:

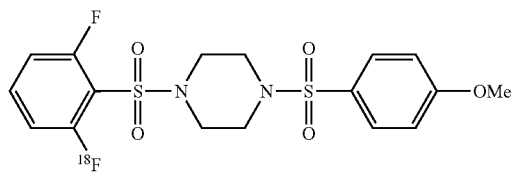

In some embodiments of this aspect of the disclosure, the method can further comprise the step of delivering the pharmaceutically acceptable probe composition to a human or non-human animal.

In some embodiments of this aspect of the disclosure, in step (ii) of said method the detection of the radionuclide can be by Positron Emission Tomography (PET).

Yet another aspect of the disclosure encompasses embodiments of a method of detecting in a human or non-human animal a localized population of cancer cells expressing pyruvate kinase M2 (PKM2), said method comprising the steps of: (i) administering to a human or non-human animal a pharmaceutically acceptable composition comprising a radiolabeled pyruvate kinase M2 (PKM2)-specific probe having the formula I:

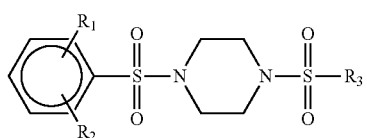

wherein $R_2$ is $^{18}$F and $R_1$ is F or $^{18}$F; and $R_3$ is a substituted aryl, naphthalene, or 1,4 benzodioxane; and (ii) identifying a tissue in the animal or human host, wherein the amount of the detectable label in the tissue is greater than in other tissues of the host, thereby identifying a population of cancer cells expressing pyruvate kinase M2.

In some embodiments of this aspect of the disclosure, the probe can have the formula IV:

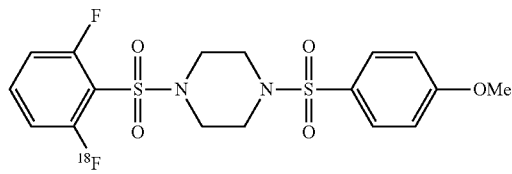

In some embodiments of this aspect of the disclosure, the radiolabeled pyruvate kinase M2 (PKM2)-specific probe can be detected by Positron Emission Tomography (PET) scanning.

In some embodiments of this aspect of the disclosure, the tissue is a glioma of the brain.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Example 1

Cell culture: HeLa cells (ATCC) and U87 human glioma cells (ATCC) were grown in Dulbecco modified Eagle medium (DMEM; Life Technologies), containing 10% FBS, 2 mM L-glutamine and 2.5 mL penicillin/streptomycin (100 $IU \cdot mL^{-1}/100$ $mg \cdot mL^{-1}$).

GBM39 was transfected with a lentiviral vector that expressed a fusion protein of GFP and firefly luciferase. GBM39 cells were grown in a defined, serum-free medium consisting of a 1:1 mixture of Neurobasal-A Medium DMEM/F12 that also contained HEPES Buffer Solution (10 mM), MEM sodium pyruvate solution (1 mM), MEM non-essential amino acids solution 10 mM (1×), GlutaMAX-I Supplement (1×), and antibiotic-antimycotic (1×) from Life Technologies Inc. The full working medium was additionally supplemented with H-EGF (20 ng/mL), H-FGF-basic-154 (20 ng/mL), H-PDGF-AA (10 ng/mL), H-PDGF-BB (10 ng/mL), and heparin solution, 0.2% (2 μg/mL) as growth factors (all from Shenandoah Inc.) and B-27 (Life Technologies Inc.). All cells were incubated at 37° C. in a humidified atmosphere containing 5% $CO_2$.

Example 2

Chemicals were purchased from Aldrich chemical company (Milwaukee, Wis.). 1-((2-fluoro-6-nitrophenyl)sulfonyl)-4-((4-methoxyphenyl)sulfonyl)piperazine was prepared from 4-methoxybenzenesulfonyl chloride (Boxer et al., 2010) *J. Med. Chem.* 53: 1048-1055). Cold DASA-23 standard was also prepared according to (Boxer et al., 2010) *J. Med. Chem.* 53: 1048-1055).

Carrier-free [$^{18}$F]fluoride was prepared by the $^{18}$O (p,n)$^{18}$F nuclear reaction on a GE PETtrace cyclotron. [$^{18}$F]Fluoride drying and synthesis of crude [$^{18}$F]PKM2 were completed in the GE TRACERlab FX-FN automated synthesis module.

High-performance liquid chromatography (HPLC) grade acetonitrile ($CH_3CN$) and Millipore 18-mΩ water were used for [$^{18}$F]DASA-23 purifications which were performed on a Dionex Summit HPLC system (Dionex Corporation, Sunnyvale, Calif.) equipped with a 340-U 4-channel UV-Vis absorbance detector and radioactivity detector (Carroll & Ramsey Associates, model 105S, Berkeley, Calif.). UV detection wavelengths were 218 nm, 254 nm, and 280 nm for all the experiments. Semi-preparative HPLC reverse-phase column (Phenomenex Gemini, C18, 250×10 mm, 5 μM) was used for purification of [$^{18}$F]DASA-23. The mobile phase for the purification of [$^{18}$F]DASA-23 was water and acetonitrile. Radioactivity measurements were performed by A CRC-15R PET dose calibrator (Capintec Inc., Ramsey, N.J.). Electron spray ionization mass spectrometry was done by Vincent Coates Foundation Mass Spectrometry Laboratory, Stanford University. $^1$H and $^{19}$F nuclear magnetic resonance (NMR) spectra were taken on an Agilent 400-MHz spectrometer.

Example 3

Tert-Butyl 4-((4-Methoxyphenyl)Sulfonyl)Piperazine-1-Carboxylate (8): 1-Boc-piperazine (500 mg, 2.68 mmol, 1 equiv.) was suspended in dichloromethane (10 ml) and cooled (0° C.). Triethylamine (747 μl, 5.37 mmol, 2.0 equiv.) was added, followed by the addition of 4-methoxybenzenesulfonyl chloride (609 mg, 2.95 mmol, 1.1 equiv.). The reaction was maintained at 0° C. for 1 h and then quenched with saturated aqueous ammonium chloride (about 5 ml). The organic layer was washed with saturated ammonium chloride (2×10 ml), brine (10 ml), dried over sodium sulfate, and concentrated under reduced pressure. The crude residue was subsequently purified by flash chromatography on silica eluting with hexane-ethyl acetate (65:35) to give tert-butyl 4-((4-methoxyphenyl)sulfonyl)piperazine-1-carboxylate (8) (396 mg, 42% yield) as a colorless solid: δH (400 MHz, $CDCl_3$)=7.68 (2H, d, J 9.2 Hz), 7.0 (2H, d, J 9.2 Hz), 3.86 (3H, s), 3.90 (4H, m), 2.94 (4H, m).

Example 4

1-((4-Methoxyphenyl)Sulfonyl)Piperazine (9): Tert-butyl 4-((4-methoxyphenyl)sulfonyl)piperazine-1-carboxylate (180 mg, 0.51 mmol) was dissolved in dichloromethane (3 ml) and cooled to 0° C. Trifluoroacetic acid (TFA) (1 ml) was added, and after 1 h, the reaction was removed from the ice bath and the solvents removed in vacuo to yield the TFA salt of 1-((4-methoxyphenyl)sulfonyl)piperazine (9), which was used in the next step without purification.

Example 5

1-((2-Fluoro-6-Nitrophenyl)Sulfonyl)-4-((4-Methoxyphenyl)Sulfonyl)Piperazine (10): The oily residue (9) was dissolved in dichloromethane (5 ml) and cooled to 0° C. Triethylamine (258 μl, 1.85 mmol, 4 equiv.) was added, followed by the addition of 2-fluoro-6-nitrobenzenesulfonyl chloride (109 mg, 0.46 mmol, 1 equiv.). After 1 h, the reaction was quenched with addition of saturated aqueous ammonium chloride (about 5 ml). The organic layer was washed with saturated aqueous ammonium chloride (2×10 ml), brine (10 ml), dried over sodium sulfate, and concentrated under reduced pressure. The crude residue was dissolved in DMSO and purified by reversed-phase HPLC to yield 1-((2-fluoro-6-nitrophenyl)sulfonyl)-4-((4-methoxyphenyl)sulfonyl)piperazine (10) (180 mg, 85%) as a colorless solid: δH (400 MHz, $CDCl_3$)=7.67 (3H, m), 7.40 (1H, t, J 8.8 Hz), 7.33 (1H, d, J 8.0 Hz), 7.01 (2H, d, J 8.8 Hz), 3.89 (3H, s), 3.49 (4H, m), 3.11 (4H, m); m/z (ESI) 459 ([M+H]+, 100).

Example 6

1-((2,6-Difluorophenyl)Sulfonyl)-4-Methoxyphenyl)Sulfonyl)Piperazine (1, DASA-23) The oily residue (9) was dissolved in dichloromethane (5 ml) and cooled to 0° C. Triethylamine (258 µl, 1.85 mmol, 4 equiv.) was added followed by aliquot addition of 2,6-difluoronitrobenzenesulfonyl chloride (109 mg, 0.46 mmol, 1 equiv.). The reaction was monitored by TLC and showed completion after 1 h. The reaction was quenched with saturated aqueous ammonium chloride (approximately 5 ml). The organic layer was washed twice with saturated aqueous ammonium chloride, once with brine, dried over sodium sulfate, concentrated in vacuo, and then dissolved in DMSO and purified by reversed-phase HPLC to yield 1-((2,6-di fluorophenyl) sulfonyl)-4-((4-methoxyphenyl)sulfonyl)piperazine (1, DASA-23) (152 mg, 77%) as a colorless solid: δH (400 MHz, $CDCl_3$)=7.67 (2H, d, J 8.8 Hz), 7.54 (1H, m), 7.03 (4H, m), 3.89 (3H, s), 3.38 (4H, m), 3.11 (4H, m); m/z (ESI) 430 ([M+H]$^+$, 100).

Example 7

1-((2-Fluoro-6-(Fluoro-$^{18}$F)Phenyl)Sulfonyl)-4-((4-Methoxyphenyl)Sulfonyl)Piperazine ([$^{18}$F]DASA-23): No carrier-added aqueous [$^{18}$F]fluoride ion was produced on a PETtrace cyclotron (GE Healthcare, Sweden) by irradiation of a 1.6 ml water target using a 16 MeV proton beam on 95% enriched [$^{18}$O]$H_2O$ by the [$^{18}$O(p,n)$^{18}$F] nuclear reaction. [$^{18}$F]Fluoride in [$^{18}$O]$H_2O$ was transferred to a GE TRAC-ERlab FXFN synthesizer and trapped on an anion exchange resin (QMA cartridge in carbonate form). [$^{18}$F]Fluoride ions were then eluted into the reactor using an eluent solution containing 3.5 mg of $K_2CO_3$ and 15 mg of Kryptofix 2.2.2 (K2.2.2: 4,7,13,16,21,24-hexaoxa-1,10-diazabicyclo[8.8.8] hexacosan) in acetonitrile (0.9 ml) and water (0.1 ml). The solution was then azeotropically dried at 65° C. under helium flow and vacuum, followed by heating at 88° C. under vacuum. Nitro precursor (10) (300 µg) was dissolved in N,N-dimethylformamide (DMF) (1 ml) and added to the dry Kryptofix 2.2.2/K$^+$[$^{18}$F$^-$] complex, and the mixture was allowed to react at 110° C. for 20 min. After cooling to 40° C., the reaction mixture was diluted with sterile water (7 ml) and passed through a C18 Sep-Pak cartridge. The radiolabeled product was subsequently eluted from the C18 Sep-Pak with acetonitrile (1.5 ml) and sterile water (1.5 ml). The resulting crude mixture was then injected onto a HPLC Phenomenex Gemini C18, 5-µm (10×250 mm) semi-preparative reversed-phase column. A mobile phase of $H_2O$ (0.1% TFA)/acetonitrile (0.1% TFA) was used with a flow rate of 3.0 ml/min, and the retention time (tR) of [$^{18}$F] DASA-23 was 17.8 min. The radioactive peak corresponding to [$^{18}$F]DASA-23 was diluted in a round-bottom flask containing sterile water (20 ml) and then trapped on a C18 Sep-Pak. The trapped, purified radiolabeled product was eluted from the C18 Sep-Pak using ethanol (1 ml) and saline (9 ml). The formulated product was then transferred into a sterile, pyrogen-free 30-ml vial. The radiochemical yield was 2.61±1.54% (non-decay corrected at end of synthesis (EOS)) with a specific activity of 2.59±0.44 Ci/µmol (n=10) and purity greater than 95%. The chemical and radiochemical purities were determined by reversed-phase analytical HPLC Phenomenex Gemini C-18, 5 µm (4.6×250 mm). A mobile phase of $H_2O$ (0.1% TFA)/acetonitrile (0.1% TFA) was used with a flow rate of 1.0 ml/min, and tR of [$^{18}$F] DASA-23 was 10.3 min.

Example 8

Cell Uptake Studies: HeLa cells (0.5×106) were plated into 6-well plates overnight before [$^{18}$F]DASA-23 uptake analysis. On the day of the experiment, fresh, prewarmed DMEM containing 25 µCi of [$^{18}$F]DASA-23 was added to individual wells (1 ml per well). Cells were incubated with [$^{18}$F]DASA-23 at 37° C. and 5% $CO_2$ over a 60 min time course. For blocking studies, TEPP-46 (Cayman Chemical, 0.25 µM, at a final concentration of 0.9% DMSO) was added to Hela cells straight after [$^{18}$F]DASA-23 addition and cells were incubated for 30 min. At the specified time points, incubation plates were put on ice, washed with ice-cold phosphate-buffered saline (PBS) (3×500 µl), and lysed in radioimmunoprecipitation assay buffer (Thermo Fisher Scientific Inc.; 500 µl). A portion of the cell lysates (200 µl) were used to determine the amount of decay-corrected radioactivity on a gamma counter (Cobra II Auto-Gamma Counter; Packard Biosciences Co.). The remaining cell lysate was used post radioactive decay for determination of protein concentration using a bicinchoninic acid (BCA) assay (Thermo Fisher Scientific Inc.). Additionally, 10 µl standards from the solution of [$^{18}$F]DASA-23 in DMEM (25 µCi/mi) were counted to quantitate the percentage of radiotracer uptake. For efflux studies, HeLa cells were incubated with [$^{18}$F]DASA-23 for 60 min and then washed with room temperature Hanks' buffered salt solution (3×500 µl); a subsequent incubation was then completed at 37° C. in fresh, prewarmed radiotracer-free DMEM. At the specified times, samples were processed as described above.

Example 9

In Vitro Serum Stability Studies: Human and mouse serum (Sigma-Aldrich) were centrifuged at 4° C., with speed of 13,000 rpm for 10 min. Formulated [$^{18}$F]DASA-23 (130-150 µCi, 20 µl volume) was added to 330 µl of supernatant. For control, the same volume of radiolabeled compound in 330 µl PBS was used. After vortexing the radiolabeled mixtures, 70 µl aliquots were incubated at 37° C. At predetermined time points (0, 15, 30, 60, and 120 min), 140 µl of ice-cold acetonitrile was added to corresponding samples to stop metabolism. After vortexing and centrifuging samples (10 min, 13,000 rpm), the supernatants were analyzed by analytical HPLC using the same conditions described above.

Example 10

Figure 5:
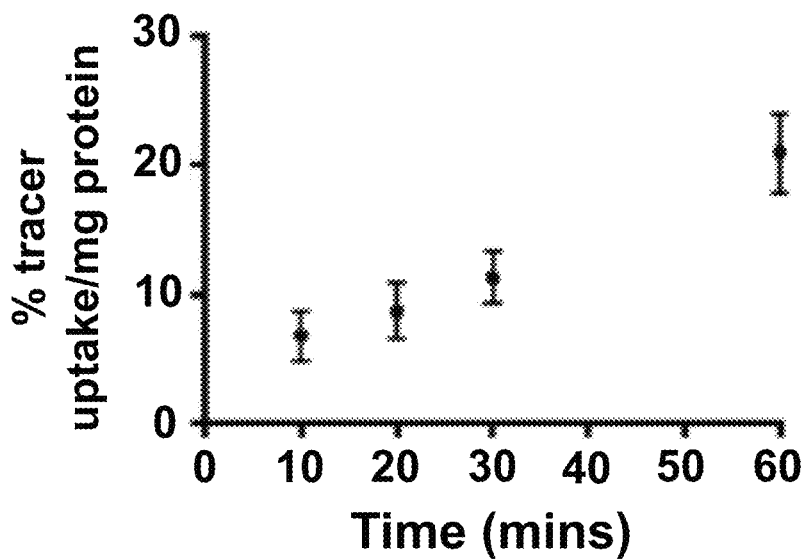
FIG. 5 illustrates cell uptake of [$^{18}$F]DASA-23 by human HeLa cervical adenocarcinoma cells. Data is mean±SD (n=2, samples run in triplicate for each experiment).
Figure 6:
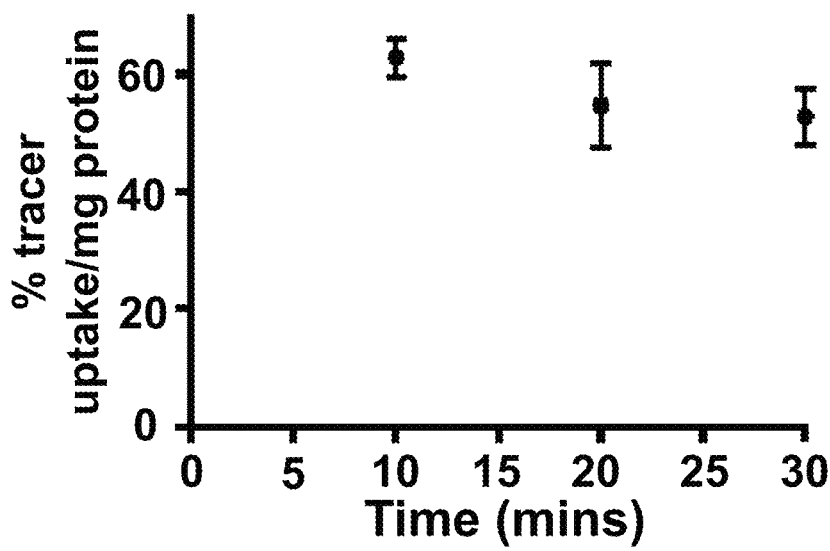
FIG. 6 illustrates washout or efflux of [$^{18}$F]DASA-23 from human HeLa cervical adenocarcinoma cells. Data is mean±SD (n=2, samples run in triplicates for each experiment).
Figure 7:
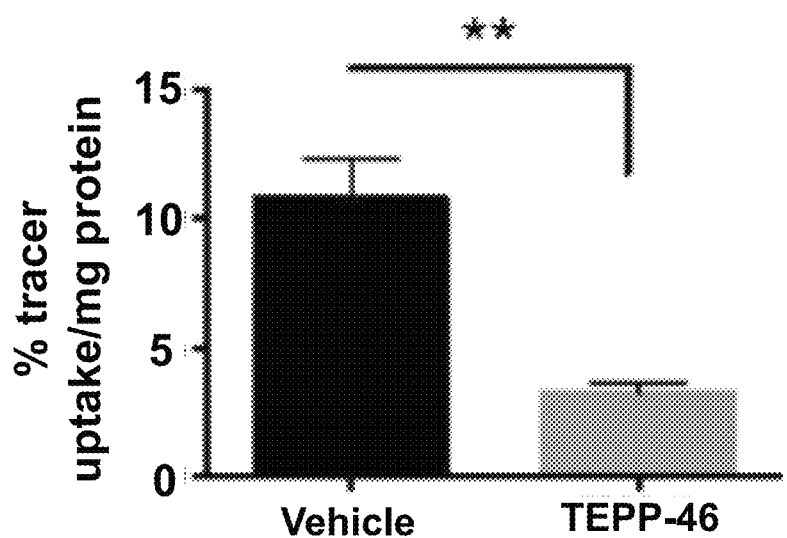
FIG. 7 is a bar graph illustrating the specificity of [$^{18}$F] DASA-23 uptake in HeLa cells assessed by coincubating cells with TEPP-46 for 30 min. Data are means±SD (n=2 separate experiments, samples were run in triplicates for each experiment). **$p<0.01$.

Cell Uptake Studies: Cell culture studies showed rapid cellular uptake of the tracer in HeLa tumor cells post addition of [$^{18}$F]DASA-23, with uptake values of 11.4±2.2 and 21.0±2.0% of total tracer/mg protein at 30 and 60 min, respectively (as shown in FIG. 4). Removal of tracer from the cell media resulted in some efflux of the cell-associated radioactivity with 52.8±4.8% of tracer still retained 30 min after removal of the [$^{18}$F]DASA-23 from media (as shown in FIG. 5). Upon addition of TEPP-46, a structurally different class of PKM2 activator, which binds to the same allosteric site as the DASA-23 class of compounds, significant blocking (70%, p<0.01) of tracer uptake was observed (as shown in FIGS. 5-7).

Example 11

Figure 8:
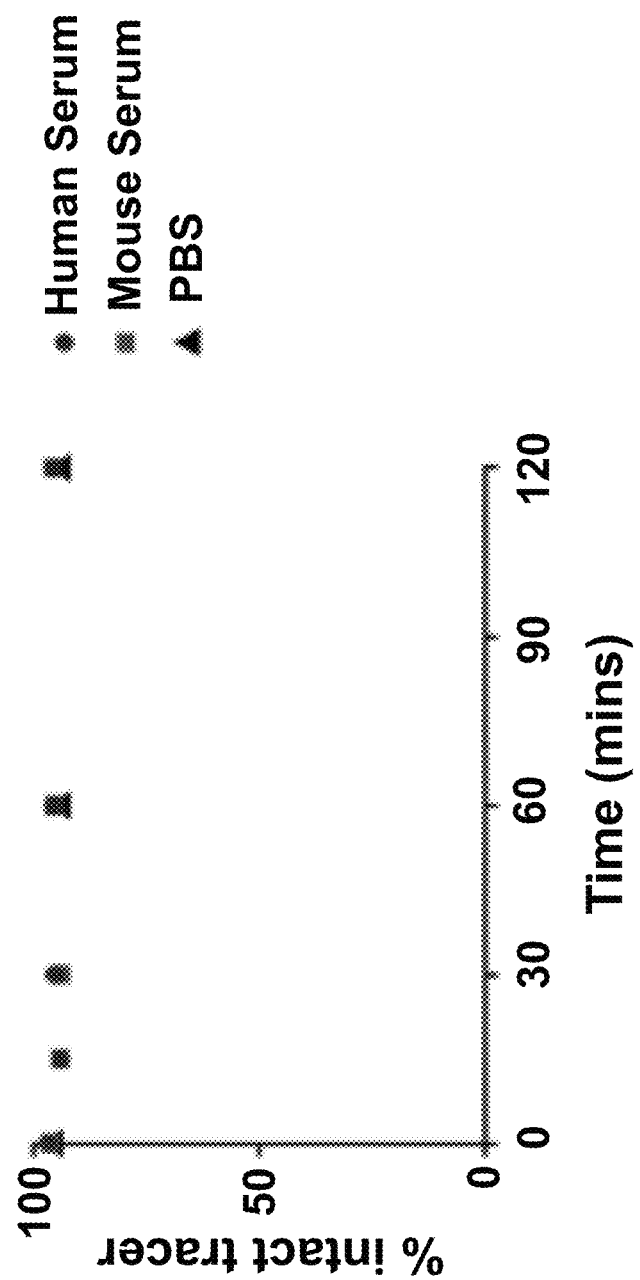
FIG. 8 is a graph illustrating in vitro human and mouse serum stability of [$^{18}$F]DASA-23 by the percentage of intact tracer over time.
Figure 9A:
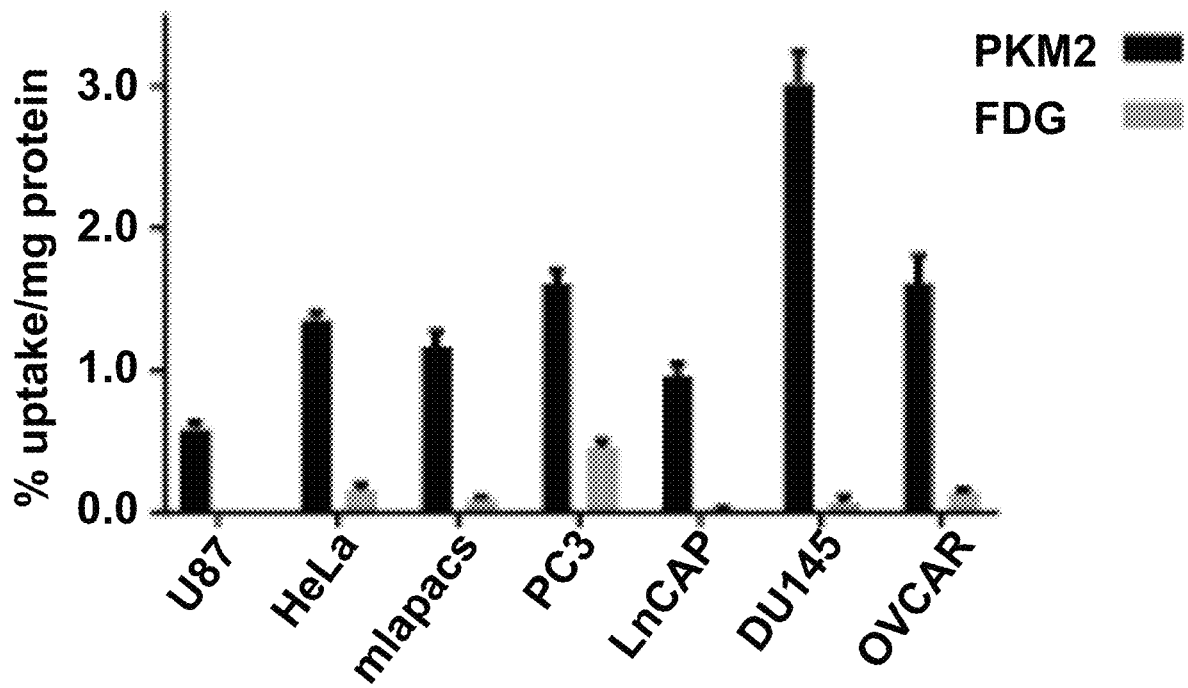
FIG. 9A illustrates the cell uptake profile of [$^{18}$F]DASA-23 after 30 min compared to [18F]FDG in a panel of cancer cell lines: U87, human glioblastoma; HeLa, human cervical adenocarcinoma; MiaPACA, human pancreatic cancer; LnCAP, DU145 and PC3, human prostate cancer.
Figure 9B:
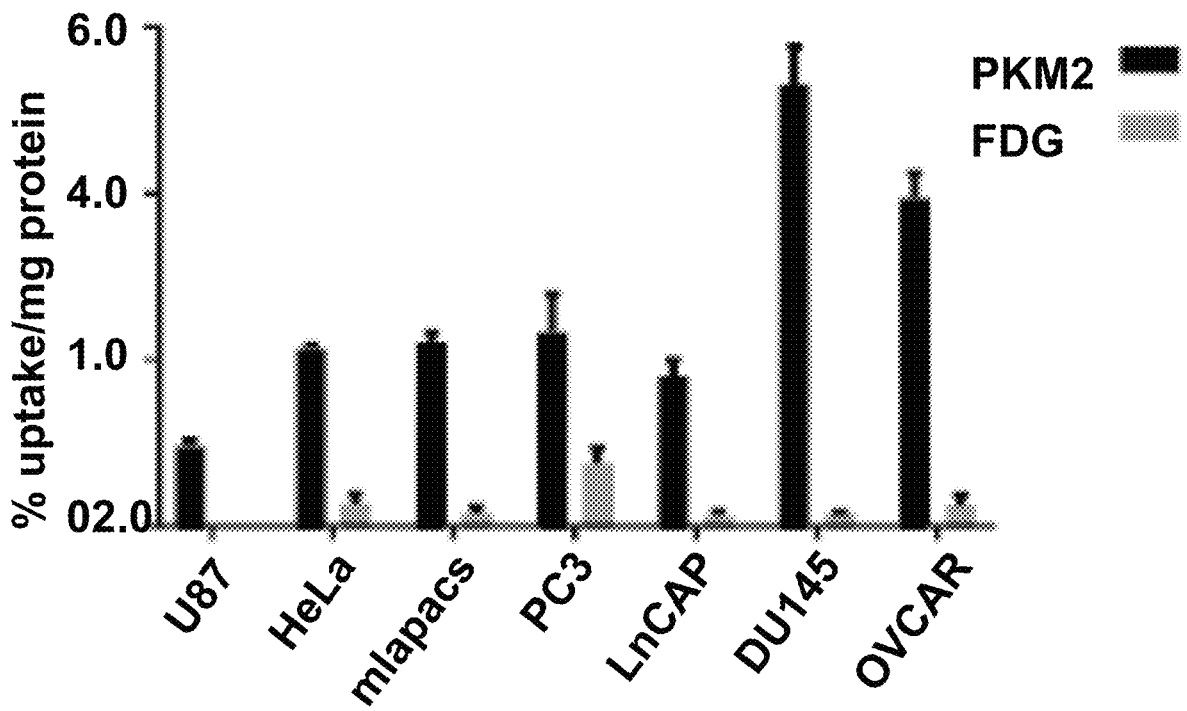
FIG. 9B illustrate the cell uptake profile of [$^{18}$F]DASA-23 after 60 min compared to [18F]FDG in a panel of cancer cell lines: U87, human glioblastoma; HeLa, human cervical adenocarcinoma; MiaPACA, human pancreatic cancer; LnCAP, DU145 and PC3, human prostate cancer.
Figure 10:
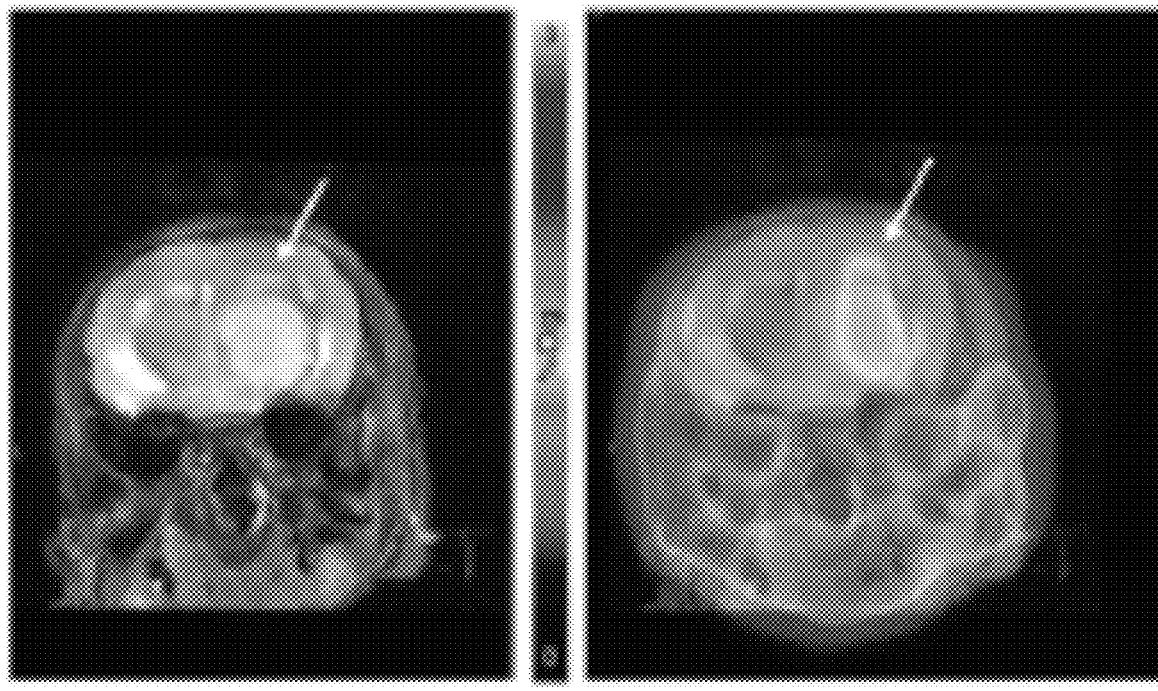
FIG. 10 illustrates non-invasive imaging of mice bearing orthotopic U87 tumor showing representative T2-weighted MR image and fused PET/CT/MR (10 to 30 min summed activity) of a mouse head bearing an orthotopically grown U87 tumor, white arrows indicate the tumor.
Figure 11:
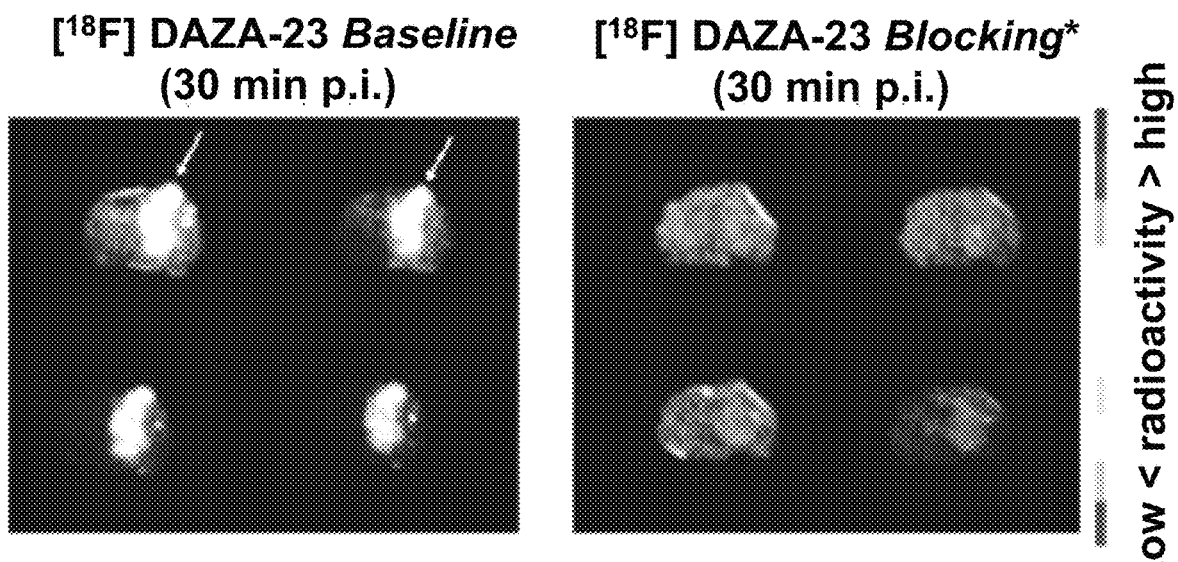
FIG. 11 illustrates non-invasive imaging of mice bearing orthotopic U87 tumor showing an ex vivo autoradiography of coronal mouse brain sections. Baseline study involved injection of radiotracer only ([$^{18}$F]DASA-23, 200 µCi), whereas the blocked study involved pre-treatment with structurally distinct PKM2 activator TEPP-46 (50 mg/kg) 60 min prior to [$^{18}$F]DASA-23 radiotracer administration.

Stability Studies: In vitro plasma stability studies showed that [18F]DASA-23 was stable following incubation with either human or mouse serum at 37° C. for up to 120 min. The percentage of intact [$^{18}$F]DASA-23 was 95.7 and 95.8 for respective incubation with human and mouse serum (FIG. 8).

Example 12

Chemistry: Scheme 1 (FIG. 2) illustrates the synthesis of 1-((2-fluoro-6-nitrophenyl)sulfonyl)-4-((4-methoxyphenyl) sulfonyl)piperazine (10), the [18F]DASA-23 precursor. The synthesis begins with reaction of commercially available 4-methoxybenzenesulfonyl chloride with tert-butyl piperazine-1-carboxylate to afford inter-mediate compound 8. Cleavage of the boc-protecting group and subsequent reaction with 3-fluoro-5-nitrobenzenesulfonyl chloride afford the desired precursor 10 in 36% yield over three steps.

Figure 3:
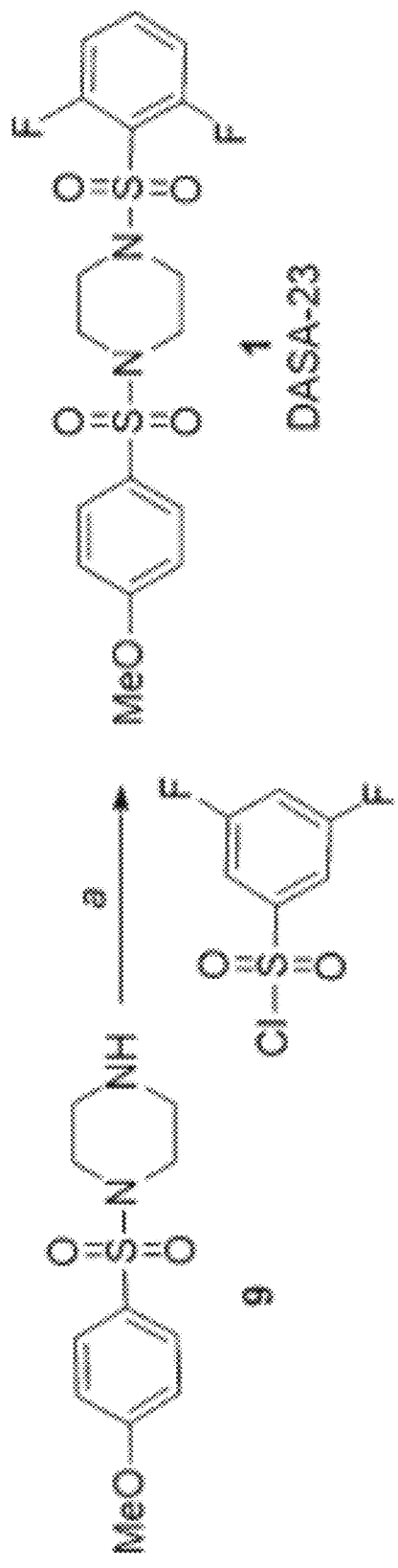
FIG. 3 illustrates scheme 2 for the synthesis of DASA-23 cold standard. Reagents and conditions. a $NEt_3$, $CH_2Cl_2$, 0° C., 1 h, 77%.

Scheme 2 (FIG. 3) describes the synthesis of cold DASA-23 standard (1) which is readily prepared via reaction of previously synthesized intermediate compound 8 with 3,5-difluorobenzenesulfonyl chloride.

Radiochemistry: [$^{18}$F]DASA-23 (1) (Scheme 3) (FIG. 4) was prepared by nucleophilic displacement of the nitro group within 10 by the [$^{18}$F]fluoride ion in DMF at 110° C. for 20 min. Subsequent purification by semi-preparative HPLC yielded pure [$^{18}$F]DASA-23. The radiochemical yield was 2.61±1.54%, non-decay corrected at EOS, and the specific activity was 2.59±0.44 Ci/μmol (n=10). The identity of [$^{18}$F]DASA-23 was confirmed by analytical HPLC coinjection with cold standard.

Example 13

General Scheme for Synthesis of Alternative Derivatives

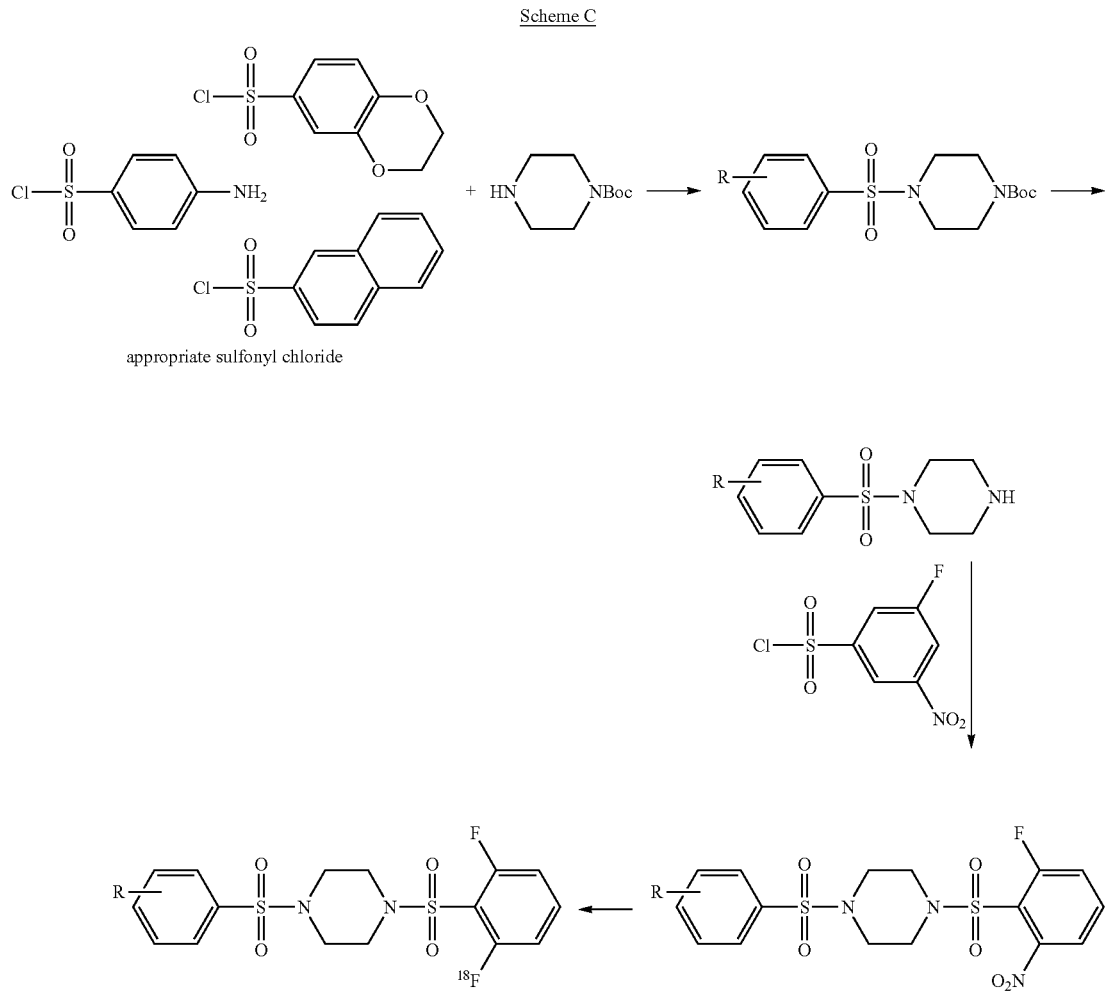

What is claimed:

1. A pyruvate kinase M2 activator precursor having the formula I:

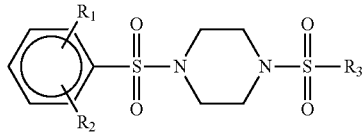

wherein:
  at least one of $R_1$ and $R_2$ is $NO_2$,
  when $R_2$ is $NO_2$, $R_1$ is F or $NO_2$; and
  $R_3$ is a substituted aryl, naphthalene, or 1,4 benzodioxane.

2. The pyruvate kinase M2 activator precursor of claim 1, wherein $R_3$ is an alkoxyphenyl or an aminophenyl.

3. The pyruvate kinase M2 activator precursor of claim 1, wherein $R_3$ is 4-methoxyphenyl, 4-ethoxyphenyl, 4-propoxyphenyl, or 4-aminophenyl.

4. The pyruvate kinase M2 activator precursor of claim 1, wherein said precursor has the formula II:

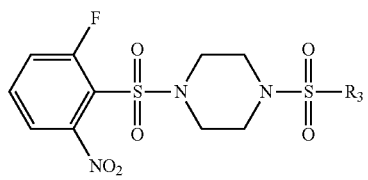

wherein $R_3$ is a substituted aryl.

5. The pyruvate kinase M2 activator precursor of claim 4, wherein $R_3$ is 4-methoxyphenyl.

6. A Positron Emission Tomography (PET)-detectable probe having the formula III:

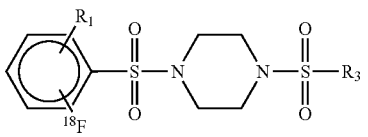

wherein:
  $R_1$ is F or $^{18}F$; and
  $R_3$ is a substituted aryl, naphthalene, or 1,4 benzodioxane.

7. The Positron Emission Tomography (PET)-detectable probe of claim 6, wherein $R_3$ is an alkoxyphenyl or an aminophenyl.

8. The Positron Emission Tomography (PET)-detectable probe of claim 7, wherein $R_3$ is 4-methoxyphenyl, 4-ethoxyphenyl, 4-propoxyphenyl, or 4-aminophenyl.

9. The Positron Emission Tomography (PET)-detectable probe of claim 8, wherein said precursor has the formula IV:

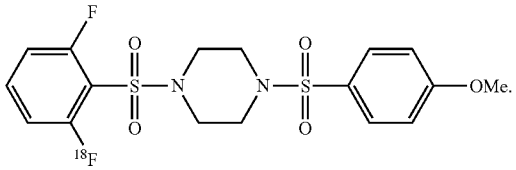

10. A pharmaceutically acceptable probe composition comprising a Positron Emission Tomography (PET)-detectable radiolabelled probe having the formula III:

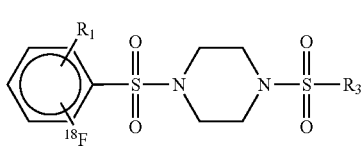

wherein:
  $R_1$ is F or $^{18}F$; and
  $R_3$ is a substituted aryl, naphthalene, or 1,4 benzodioxane.

11. The pharmaceutically acceptable probe composition of claim 10 comprising a Positron Emission Tomography (PET)-detectable radiolabelled probe having the formula IV:

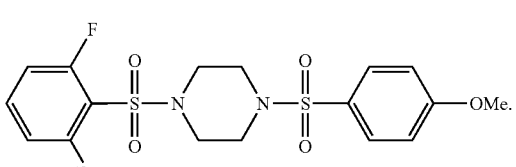

12. The pharmaceutically acceptable probe composition of claim 10, further comprising a pharmaceutically acceptable carrier.

13. A method of generating a pyruvate kinase M2 activator precursor, wherein said precursor is 1-((2-fluoro-6-nitrophenyl)sulfonyl)-4-((4-methoxyphenyl)sulfonyl)piperazine (10) having the formula II:

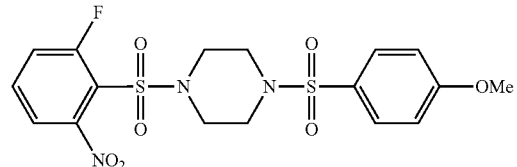

the method comprising the steps of:
  (a) reacting 1-Boc-piperazine, trimethylamine and 4-methoxybenzenesulfonyl chloride to generate tert-butyl 4-((4-methoxyphenyl)sulfonyl)piperazine-1-carboxylate (8);
  (b) quenching the reaction of step (a) with saturated aqueous ammonium chloride and purifying the first product;

(c) reacting the product of step (b) with trifluoroacetic acid to generate a TFA salt of 1-((4-methoxyphenyl)sulfonyl)piperazine (9); and (d) reacting the TFA salt of 1-((4-methoxyphenyl)sulfonyl)piperazine (9) product of step (c) with 2-fluoro-6-nitrobenzenesulfonyl chloride to generate 1-((2-fluoro-6-nitrophenyl)sulfonyl)-4-((4-methoxyphenyl)sulfonyl)piperazine (10) or with 2-bromo-6-fluorobenzenesulfonyl chloride to generate 1-((2-bromo-6-fluorobenzenesulfonyl)-4-((4-methoxyphenyl)sulfonyl)piperazine.

14. The method of claim 13, wherein step (d) comprises reacting the TFA salt of 1-((4-methoxyphenyl)sulfonyl)piperazine (9) product of step (c) with 2-fluoro-6-nitrobenzenesulfonyl chloride to generate 1-((2-fluoro-6-nitrophenyl)sulfonyl)-4-((4-methoxyphenyl)sulfonyl)piperazine (10).

15. A method of generating a radiolabelled probe, wherein the probe is 1-((2-fluoro-6-(fluoro-$^{18}$F)phenyl)sulfonyl)-4-((4-methoxyphenyl)sulfonyl)piperazine, said method comprising the steps:

(a) fluoridating 4,7,13,16,21,24-hexaoxa-1,10-diazabicyclo[8.8.8]hexacosan (K2.2.2) with $^{18}$F; and (b) reacting 1-((2-fluoro-6-nitrophenyl)sulfonyl)-4-((4-methoxyphenyl)sulfonyl)piperazine (10) or 1-((2-bromo-6-fluorobenzenesulfonyl)-4-((4-methoxyphenyl)sulfonyl)piperazine with the fluoridated product of step (a), thereby obtaining 1-((2-fluoro-6-(fluoro-$^{18}$F)phenyl)sulfonyl)-4-((4-methoxyphenyl)sulfonyl)piperazine.

16. The method of claim 15, wherein step (b) comprises reacting 1-((2-fluoro-6-nitrophenyl)sulfonyl)-4-((4-methoxyphenyl)sulfonyl)piperazine (10) with the fluoridated product of step (a), thereby obtaining 1-((2-fluoro-6-(fluoro-$^{18}$F)phenyl)sulfonyl)-4-((4-methoxyphenyl)sulfonyl)piperazine.

17. A method of detecting a cell or a population of cells expressing pyruvate kinase M2, said method comprising:

(i) contacting a cell or population of cells with a pharmaceutically acceptable PET-detectable radiolabelled probe composition comprising at least one probe having a radionuclide and having the formula I:

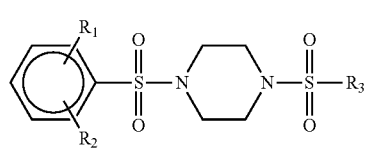

I wherein $R_2$ is $^{18}$F and $R_1$ is F or $^{18}$F; and $R_3$ is a substituted aryl, naphthalene, or 1,4 benzodioxane; and (ii) detecting pyruvate kinase M2-specific binding of the radionuclide-containing probe within the cell or population of cells by detecting the presence of the radionuclide in the cell or population of cells.

18. The method of claim 17, wherein the probe has the formula IV:

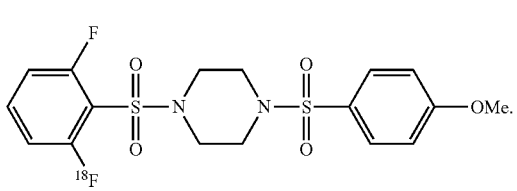

IV

19. The method of claim 17, further comprising the step of delivering the pharmaceutically acceptable probe composition to a human or non-human animal.

20. The method of claim 17, wherein in step (ii), the detection of the radionuclide is by Positron Emission Tomography (PET).

21. A method of detecting in a human or non-human animal a localized population of cancer cells expressing pyruvate kinase M2 (PKM2), said method comprising the steps of:

(i) administering to a human or non-human animal a pharmaceutically acceptable composition comprising a radiolabeled pyruvate kinase M2 (PKM2)-specific probe having the formula I:

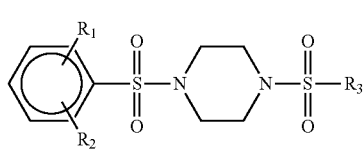

I wherein $R_2$ is $^{18}$F and $R_1$ is F or $^{18}$F; and $R_3$ is a substituted aryl, naphthalene, or 1,4 benzodioxane; and (ii) identifying a tissue in the animal or human host, wherein the amount of the detectable label in the tissue is greater than in other tissues of the host, thereby identifying a population of cancer cells expressing pyruvate kinase M2.

22. The method of claim 21, wherein the probe has the formula IV:

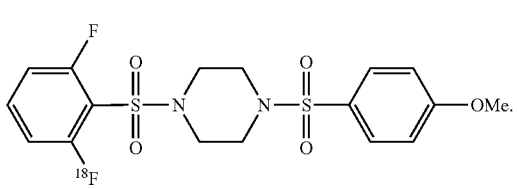

IV

23. The method of claim 20, wherein the radiolabeled pyruvate kinase M2 (PKM2)-specific probe is detected by Positron Emission Tomography (PET) scanning.

24. The method of claim 20, wherein the tissue is a glioma of the brain.

* * * * *